(12) United States Patent
Iaccino et al.

(10) Patent No.: US 8,378,162 B2
(45) Date of Patent: Feb. 19, 2013

(54) PROCESS FOR METHANE CONVERSION

(75) Inventors: Larry L. Iaccino, Seabrook, TX (US); Steven E. Silverberg, Seabrook, TX (US); James R. Lattner, LaPorte, TX (US); Andrea P. Wight, Huffman, TX (US); Garth M. Norman, Houston, TX (US); Douglas E. Smith, The Woodlands, TX (US); Eric D. Nelson, Stavanger (NO); Mark A. Nierode, Houston, TX (US); Moses K. Minta, Missouri City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 369 days.

(21) Appl. No.: 12/718,712

(22) Filed: Mar. 5, 2010

(65) Prior Publication Data

US 2010/0256245 A1    Oct. 7, 2010

Related U.S. Application Data

(60) Provisional application No. 61/160,102, filed on Mar. 13, 2009.

(51) Int. Cl.
*C07C 1/00* (2006.01)
*C07C 27/00* (2006.01)

(52) U.S. Cl. ...................... 585/322; 518/700
(58) Field of Classification Search ........... 585/322; 518/700
See application file for complete search history.

(56) References Cited

U.S. PATENT DOCUMENTS

| | | | |
|---|---|---|---|
| 5,336,825 | A | 8/1994 | Choudhary et al. |
| 7,019,184 | B2 | 3/2006 | Allison et al. |
| 7,451,618 | B2 | 11/2008 | Ansorge et al. |
| 7,589,246 | B2 | 9/2009 | Iaccino et al. |
| 7,659,437 | B2 | 2/2010 | Iaccino et al. |
| 2007/0129587 | A1 | 6/2007 | Iaccino et al. |
| 2007/0249740 | A1 | 10/2007 | Iaccino et al. |
| 2007/0249880 | A1 | 10/2007 | Iaccino et al. |
| 2007/0260098 | A1 | 11/2007 | Iaccino et al. |
| 2007/0282145 | A1 | 12/2007 | Iaccino et al. |
| 2008/0021251 | A1 | 1/2008 | Iaccino et al. |
| 2008/0047872 | A1 | 2/2008 | Iaccino et al. |
| 2008/0051617 | A1 | 2/2008 | Sangar et al. |
| 2008/0058564 | A1 | 3/2008 | Iaccino et al. |
| 2009/0030253 | A1 | 1/2009 | Xu et al. |
| 2010/0004493 | A1 | 1/2010 | Porter et al. |

FOREIGN PATENT DOCUMENTS

| | | |
|---|---|---|
| EP | 1 306 632 | 5/2003 |
| WO | 2007/123808 | 11/2007 |
| WO | 2009/097067 | 8/2009 |
| WO | 2010/004300 | 1/2010 |

OTHER PUBLICATIONS

Wicaksono et al., *"Integrating Recovered Jetty Boil-off Gas as a Fuel in an LNG Plant"*, 17th European Symposium on Computer Aided Process Engineering-ESCAPE 17, (2007) Elsevier B.V., pp. 1-6.

*Primary Examiner* — Jafar Parsa
(74) *Attorney, Agent, or Firm* — Andrew B. Griffis

(57) ABSTRACT

The invention relates to the integration of a dehydroaromatization process with the processes for the utilization of associated gas; gases comprising methane and higher hydrocarbons, and/or liquefied natural gas (LNG) production or usage.

18 Claims, 5 Drawing Sheets

PROCESS FOR METHANE CONVERSION

CROSS REFERENCE TO RELATED APPLICATION

This application claims priority to U.S. Provisional Patent Application No. 61/160,102, filed Mar. 13, 2009, the disclosure of which is incorporated herein by reference in its entirety.

FIELD OF THE INVENTION

The invention relates to the conversion of feedstreams containing methane to aromatic hydrocarbons by dehydroaromatization and processes for the utilization of associated gas and/or liquefied natural gas (LNG) production.

BACKGROUND OF THE INVENTION

Integration of systems is per se known. By way of example, the integration of an isomerization process with a disproportionation process around a common compressor is taught in U.S. Patent Publication 2010-0004493. In another example, the preparation of liquid hydrocarbons from a light hydrocarbonaceous feedstock is combined with a process for liquefying natural gas, involving the production of syngas (CO and $H_2$), is taught in U.S. Pat. No. 7,451,618.

Aromatic hydrocarbons, particularly benzene, toluene, and xylenes (collectively, "BTX") and also ethylbenzene, are important commodity chemicals in the petrochemical industry. Currently, aromatic hydrocarbons are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane. The present inventors have noted that possible sources of methane include natural gas and biogas. More natural gas is currently being discovered than oil. Likewise, production and collection of biogas, such as from landfill (e.g., "garbage dumps") is increasing tremendously. However, there are numerous problems associated with transportation of large volumes of such gases. For instance, natural gas recovered along with oil (also known as "associated gas"), particularly at remote places, is generally flared and thus wasted. More efficient use of such gases is critical.

A large majority of the processes currently proposed for converting methane to liquid hydrocarbons involve initial oxidation of methane to synthesis gas, such as U.S. Pat. No. 7,451,618 referenced above.

In U.S. Pat. No. 7,451,618 (EP 1306632), liquid hydrocarbons are produced from a light hydrocarbonaceous feedstock in combination with a process for liquefying natural gas, which liquefaction process comprises converting a light hydrocarbonaceous feedstock into synthesis gas, followed by catalytic conversion of the synthesis gas into liquid hydrocarbons. While this application claims efficiencies associated with integration of two processes (natural gas liquefaction and liquid hydrocarbon synthesis), it is still inherently inefficient for at least two reasons, one being the large pressure differential between the liquefaction effluent stream and the preferred operating pressure for the liquid hydrocarbon synthesis, and another being that production of synthesis gas as an intermediate step in the production of liquid hydrocarbons is capital and energy intensive. Accordingly, a more efficient integration of methane conversion technologies with gas liquefaction would be of value.

A number of other processes have been proposed for directly converting methane to higher hydrocarbons, such as catalytic oxidative coupling of methane to olefins followed by the catalytic conversion of the olefins to liquid hydrocarbons, including aromatic hydrocarbons. See, for example, U.S. Pat. No. 5,336,825. However, oxidative coupling methods suffer from the problem that they involve highly exothermic reactions (and thus are exposed to potentially hazardous methane combustion reactions) and they generate large quantities of environmentally sensitive carbon oxides.

Non-oxidative coupling has also been proposed in numerous patents, typically involving contacting methane with a catalyst comprising a metal supported on a zeolite, such as ZSM-5, at high temperature, such as 600° C. to 1000° C. See, for example, patents cited in the Background section of U.S. Patent Publication 2007/0260098.

Non-oxidative coupling methods include dehydroaromatization. As used herein, the term "dehydroaromatization" means processes comprising non-oxidative coupling reactions wherein methane is converted to aromatic hydrocarbons, such as benzene, toluene, and naphthalene (commonly referred to collectively as "BTN"), along with $H_2$, using a supported metal catalyst. Syngas is not a significant intermediate. Such processes have also been referred to as dehydrocyclization, although the latter can also include (or be confused with) the production of cyclic paraffins. Such prior art dehydroaromatization processes are almost exclusively "once through" (no recycle) and do not address separation of the products.

For instance, in the aforementioned U.S. Patent Publication 2007/0260098, a process is described for converting methane to higher hydrocarbons including aromatic hydrocarbons, the process comprising contacting a feed containing methane with a catalyst useful for dehydroaromatization, conveniently molybdenum, tungsten and/or rhenium or a compound thereof on ZSM-5 or an aluminum oxide, under conditions effective to convert said methane to aromatic hydrocarbons and produce a first effluent stream comprising aromatic hydrocarbons and $H_2$, wherein said first effluent stream comprises at least 5 wt % more aromatic rings than said feed; and reacting at least part of the $H_2$ from said first effluent stream with an oxygen-containing species to produce a second effluent stream having a reduced $H_2$ content compared with said first effluent stream.

Other references pertinent to dehydroaromatization include U.S. Patent Publications 2008/0047872; 2008/0058564; 2007/0249740; 2007/0129587 (now allowed); 2007/0282145; 2008/0021251; 2008/0051617; 2007/0249880; 2007/0260098; 2009/0030253; U.S. Pat. Nos. 7,589,246 and 7,659,437; WO 2009/097067, and WO 2007/123808.

In order for a methane conversion process to be adopted on a commercial scale, most of the gas used in the process needs to be converted to high value products, such as benzene, and/or moderate to high value co-products, such as $H_2$. Without wishing to be bound by theory, based on thermodynamic considerations there is only a limited amount of the methane feed that can be converted to aromatic products, at reasonable (i.e., economically viable) operating conditions. Accordingly, the product stream contains large amounts of unreacted methane as well as $H_2$ and aromatic species. Separation of BTN and light olefin byproducts can be accomplished by methods known per se, however, separation of byproduct $H_2$ from $CH_4$ is difficult, requiring expensive equipment and high energy use.

Recovery of relatively high purity $H_2$ (low $CH_4$ content) for uses such as catalyst regeneration and/or to make syngas for methanol or other product synthesis, and likewise recovery of relatively high purity $CH_4$ (low $H_2$ content) is also needed so that it can be recycled as feed to the reactor. In addition, reactor conversion of methane to aromatic hydrocarbons is depressed by the presence of $H_2$ in the feed.

Accordingly, a more efficient process for separation of $H_2$ and $CH_4$ from each other is highly desired. Heretofore, cryogenic separation of $H_2$ and $CH_4$, although thought to be one of the more effective means of achieving the separation, was very expensive; requiring large capital expense for multiple refrigeration machines with various refrigerants (e.g., C3, C2, and C1) or very large mixed refrigerant systems. Also resultant liquid methane must be reheated back to reactor inlet temperature, which is on the order of 500° C. or higher.

Often rather than chemically converting methane to another material for transportation, it is cooled to low enough temperatures that it liquefies so that it can be transported in liquid form as LNG (Liquefied Natural Gas). With regard to gases taken at the well-head and/or biogases, extensive refrigeration is required to cool to liquefaction temperatures. The final step is pressure reduction to atmospheric pressure with auto-refrigeration and the production of a low pressure gas stream ("boil off gas" or LNG BOG). Depending on the temperature and pressure of the stream prior to the pressure reduction to atmospheric pressure with auto-refrigeration, more or less LNG BOG is produced. If there is an outlet for more LNG BOG then the cryogenic refrigeration operation will be more economically attractive, e.g., if more and/or higher use for LNG BOG can be found the temperature of the refrigeration system(s) can be raised. So, from an efficiency standpoint, when LNG BOG volume is set by the outlet (disposition) for this stream being, by way of example, fuel used by the LNG complex, this will essentially set the required temperature prior to flashing. LNG BOG must also be compressed up to approximately 350 psi for use in gas turbines to run the LNG complex. Furthermore, Jetty BOG is also produced when LNG tankers are filled and the vapor volume is displaced. LNG BOG and Jetty BOG will be referred to collectively herein as "BOG", unless otherwise specifically noted. BOG tends to be enriched in inerts (predominately $N_2$), and these inerts are practically non-condensables in the natural gas. A more efficient use of BOG is thus highly sought after.

LNG is produced in parts of the world where there are large reserves of natural gas but paradoxically little use for it. The natural gas is thus transported as LNG to locations where it can be used for heating, power generation or industrial use. However, LNG cannot be utilized in the liquid form and therefore it must be converted back to a gas at high pressure for distribution to consumers. To supply vaporized gas at pipeline pressure, a portion of the gas is burned to provide heat which is inefficient in that a portion of the gas is consumed. It would be beneficial if the gasification of LNG could be integrated with one or more other processes.

U.S. Pat. No. 7,019,184 teaches a process in which natural gas is non-oxidatively converted to aromatic liquid and is said to provide integration of the separation of wellhead fluids into associated gas and crude with blending of the aromatic liquid derived from the gas with the crude and/or integration of conversion of byproduct $H_2$ to power with non-oxidative conversion of gas to aromatic liquid. Separation of unreacted methane and recycle of the same back to the reactor is taught.

WO 2010004300 teaches a process for treating offshore natural gas. The process comprises (i) liquefying and fractionating the natural gas to generate a liquefied natural gas stream and a higher hydrocarbon stream, (ii) vapourising at least a portion of said higher hydrocarbon stream, (iii) passing the vapourised higher hydrocarbon stream and steam over a steam reforming catalyst to generate a reformed gas mixture comprising methane, steam, carbon oxides and hydrogen, (iv) passing the reformed gas mixture over a methanation catalyst to generate a methane rich gas, and (v) combining the methane-rich gas with the natural gas prior to the liquefaction step. The process requires first separating the higher hydrocarbon from the methane; then reacting the higher hydrocarbon with steam to make CO and $H_2$; then (with a second catalyst at a second set of reaction conditions) reacting the CO and $H_2$ to produce methane and water.

The present inventors have surprisingly discovered that the process of taking well-head gases to the consumer may be integrated with the production of aromatic hydrocarbons by dehydroaromatization.

SUMMARY OF THE INVENTION

The invention is directed to the integration of LNG processes, including production and uses, with a process for dehydroaromatization of hydrocarbon streams containing methane to make aromatic hydrocarbons.

The invention is also directed to the combination of processes for taking methane from the well-head to the consumer with processes for the production of aromatic hydrocarbon compounds by dehydroaromatization.

The invention is further directed to processes involving LNG and processes involving dehydroaromatization wherein said processes share at least one common apparatus and/or process step and/or process stream.

The invention also directed to a system comprising facilities for dehydroaromatization and facilities for LNG production.

The invention is also directed to the dehydroaromatization of a hydrocarbon stream comprising methane and higher hydrocarbons such as C2-C5 paraffins, e.g., associated gas, to make aromatic hydrocarbons, which in embodiments results in a net increase in the amount of methane produced.

The invention is also concerned with the separation of a mixture of $H_2$ and $CH_4$ from a dehydroaromatization zone, in embodiments wherein there is a relatively large amount of methane gas and a relatively small amount of $H_2$.

In embodiments the invention concerns a process for dehydroaromatization and the regasification of LNG, wherein the two processes utilize or are integrated around common refrigeration equipment and/or fuel gas usage.

In embodiments, the invention is directed to use of BOG as feedstream for dehydroaromatization.

In embodiments the vaporization of LNG is used for cryogenic separation of methane and hydrogen gas ($H_2$).

In an embodiment, the present invention further comprises a step of separating benzene and/or naphthalene prior to separation of $H_2$ and methane.

It is an object of the invention to provide more efficient use of the various processes involved in taking methane from the well-head to the consumer and combining these processes with the process for providing a feedstream to a dehydroaromatization reactor and producing aromatic species therefrom.

It is a still further object of the invention to provide an efficient method of separating methane and hydrogen.

These and other objects, features, and advantages will become apparent as reference is made to the following detailed description, preferred embodiments, examples, and appended claims.

BRIEF DESCRIPTION OF THE DRAWINGS

The accompanying drawings illustrate schematically various embodiments of the invention.

DETAILED DESCRIPTION

Figure 1:
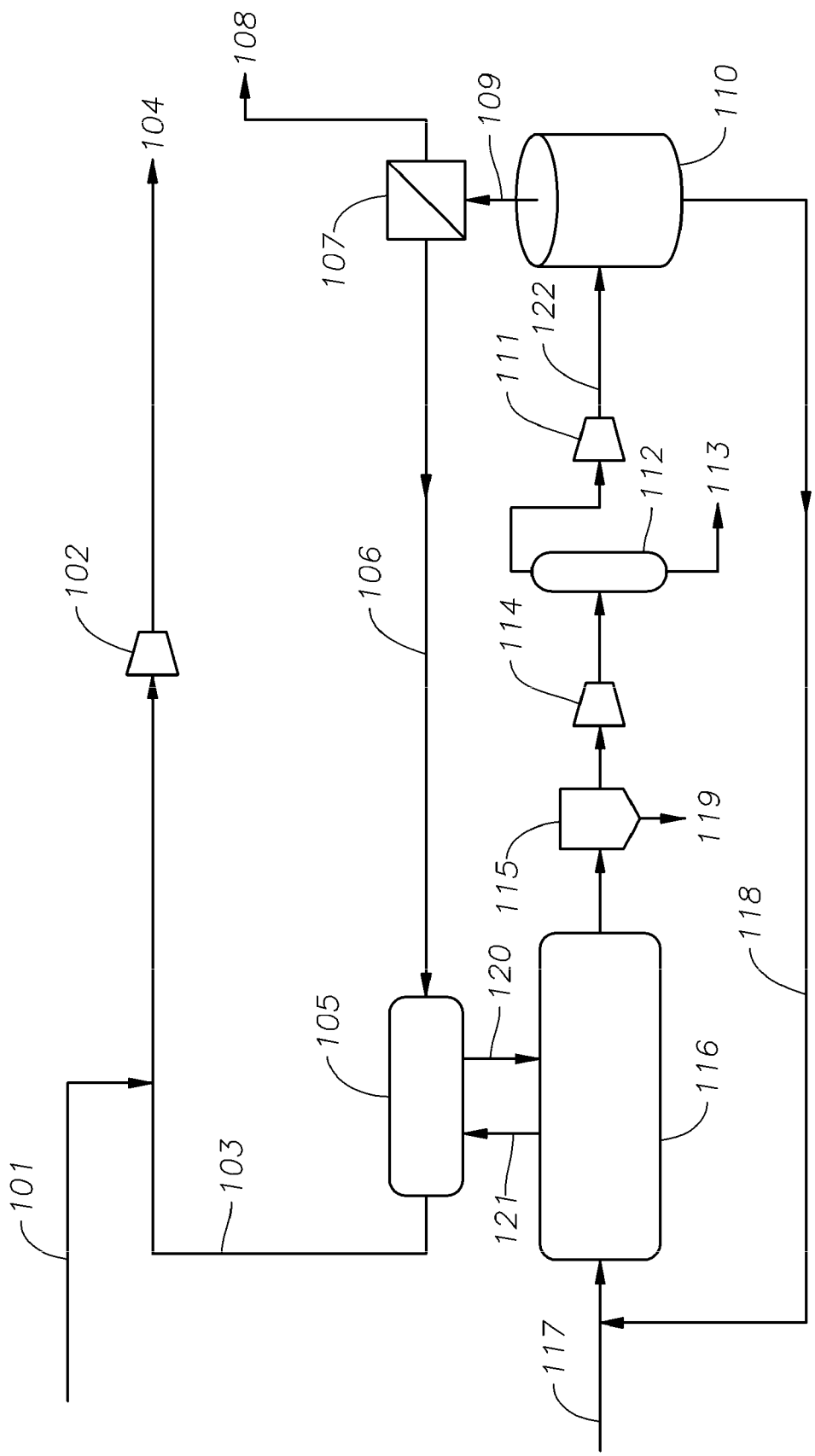
FIG. 1 is an embodiment showing a process configuration for dehydroaromatization wherein methane is cryogenically separated from $H_2$ and utilizing at least a portion of the $H_2$ to regenerate the dehydroaromatization catalyst, and at least a portion of the methane is recycled to the dehydroaromatization step.

The present invention concerns the combination or integration of dehydroaromatization and the liquefaction and use of natural gas. According to the invention, numerous efficiencies are achieved by the integration of a process to convert methane to aromatics with natural gas liquefaction or regasification facilities. As used herein the term "integration" means the combination of two or more facilities or two or more processes to improve the combined processes as a whole. It is a holistic approach to process design which considers the interactions between different unit operations from the outset, rather than optimizing them separately. The integration of processes is sometimes referred to as integrated process design or process synthesis. It is not trivial to determine the best and most technically feasible method of integrating such systems.

Accordingly, in embodiments, the invention concerns a process for converting a gaseous hydrocarbon stream comprising methane, to $H_2$ and an aromatic hydrocarbon stream comprising at least one aromatic compound, said process comprising: (a) passing said gaseous hydrocarbon stream to one or more conversion zones containing at least one dehydroaromatization catalyst under conditions suitable for converting methane to said at least one aromatic compound and $H_2$; (b) recovering said aromatic compounds thereby leaving a residual stream comprising gaseous methane and $H_2$; wherein the process is integrated with facilities for the production, transportation, or use of LNG and/or integrated with the utilization of a methane stream containing heavier hydrocarbons. In embodiments the integration or combination are with shared facilities for off- and on-loading LNG and/or cryogenic (e.g., refrigeration facilities) or warming operations and processes involved therein.

In order to better understand the present invention references will be made to numerous embodiments, which are representative of the present invention and are not intended to be limiting thereof. One of ordinary skill in the art in possession of the present disclosure will recognize that the invention may be practiced otherwise than as specifically set forth in these representative examples.

Dehydroaromatization of methane to benzene is very thermodynamically limited; only approximately 5 to 30 mol % conversion of methane to aromatic species is possible at currently feasible reactor conditions. This results in poor utilization of the methane. It would at first seem that the most desirable improvement would be to recycle the unreacted methane back to the reactor but this cannot be done without first separating out the $H_2$ byproduct from the dehydroaromatization reaction—if $H_2$ is left in the methane, it will thermodynamically suppress additional aromatics production. There are various ways of separating the methane and $H_2$, details of which are per se known in the art: membranes, adsorption, absorption, fractionation, and the like. The present inventors believed that cryogenic fractionation appeared to be the most economically attractive option even though it is still very expensive in terms of equipment requirements and energy usage.

Further evaluation of the cryogenic fractionation approach lead to the discovery that the process could be improved if, rather than regasify and recycle the methane stream from the cryogenic fractionation, we could instead leave a portion of the methane as a liquid for use as a LNG product. In embodiments, this invention allows for one or more of the following improvements: (1) realizes economy of scale on refrigeration equipment and other facilities; (2) eliminates some facilities, e.g., heat exchangers to regasify the methane if it were to be recycled; (3) allows higher pre-liquefaction flash temperature (for example >1° C. higher; preferably >5° C. higher; more preferably >10° C. higher) since more boil off gas (LNG BOG) can be generated to be used as fuel, due to higher energy demand for entire complex. A variant is to share refrigeration systems and fuel gas systems as utilities but to keep feed and higher value product process streams segregated; e.g., (1) refrigerant systems could be shared all or in part for methane liquefaction to LNG and the cryogenic fractionation of the methane+$H_2$ containing stream from dehydroaromatization; (2) streams separated to be used fuel from LNG production and streams separated to be used as fuel from the dehydroaromatization process (including recovery and regeneration) can be used as fuel for LNG production and/or for fuel for the dehydroaromatization process.

Accordingly, in embodiments the invention concerns a process for converting a gaseous hydrocarbon stream comprising methane, to LNG, a $H_2$ rich stream, and an aromatic hydrocarbon stream comprising at least one aromatic compound, said process comprising: (a) passing said gaseous hydrocarbon stream to one or more conversion zones containing at least one dehydroaromatization catalyst under conditions suitable for converting methane to said at least one aromatic compound and $H_2$; (b) recovering said aromatic compounds thereby leaving a residual stream comprising gaseous methane and $H_2$; (c) separating said methane and $H_2$ into a gaseous, $H_2$ rich stream and a liquid, methane rich stream; wherein said separating includes cryogenic separation utilizing one or more cryogenic refrigerants; (d) routing said $H_2$ rich stream to a desired disposition with or without further processing; (e) routing said liquid, methane rich stream to an LNG disposition with or without further processing.

In addition, another embodiment of the invention concerns a process for converting a gaseous hydrocarbon stream comprising methane, to LNG, a $H_2$ rich stream, and an aromatic hydrocarbon stream comprising at least one aromatic compound, said process comprising: (a) passing a first portion of said gaseous hydrocarbon stream to one or more conversion zones containing at least one dehydroaromatization catalyst under conditions suitable for converting methane to said at least one aromatic compound and $H_2$; (b) recovering said aromatic compounds thereby leaving a residual stream comprising gaseous methane and $H_2$; (c) separating said methane and $H_2$ into a $H_2$ rich stream and a methane rich stream; wherein said separating includes cryogenic separation utilizing one or more cryogenic refrigerants; (d) routing said $H_2$ rich stream to a desired disposition with or without further processing; (e) passing a second portion of said gaseous hydrocarbon stream to an LNG liquefaction process utilizing one or more cryogenic refrigerants to produce a liquid methane containing stream; (f) routing said liquid methane containing stream to an LNG disposition with or without further processing; the process further characterized in that the at least one of the one or more cryogenic refrigerants of (c) and (e) are supplied from the same refrigerant system.

One skilled in the art will recognize, once being made aware of the above information, that the above process integration would provide significant reduction in capital requirements and at least some reduction in energy use.

The present invention also concerns the use of Boil off gas (BOG) as a feed for dehydroaromatization.

As mentioned, dehydroaromatization of methane to benzene is limited by thermodynamics to only approximately 5 to 30% conversion of methane at current feasible reactor conditions. Rather than separate out the $H_2$ from the methane and recycle the methane, one could consider routing the entire methane+$H_2$ steam to fuel or other dispositions. However, in order to do this the stream must be compressed from dehydroaromatization reactor outlet pressures approximately 20 to 40 psia up to downstream consumer demand pressure approximately 300 psia or greater. Significant energy use and equipment is required to do this compression.

The present inventors have discovered that there is an opportunity to integrate this compression with existing facilities in LNG operations to significantly reduce investment and energy use. In LNG operations low pressure, near atmospheric pressure streams are generated. These may be LNG train boil off gas (LNG BOG) or loading jetty boil off gas (Jetty BOG). LNG BOG is produced when, after the final stage of heat exchange, the refrigerated stream is flashed down to near atmospheric pressure to produce a near atmospheric pressure liquid stream of LNG product and the LNG BOG. Jetty BOG is produced when LNG is in storage tanks and some liquid is converted to vapor by heat incursion into the tank or when LNG is loaded into stationary or on-ship tanks and vapor is created due to displacement of inert blanket that is previously in the tank as well as by vaporization caused if the tank is at a temperature greater than the LNG. BOG typically contains 85 to 95 mol % methane and 10 to 15 mol % nitrogen. The BOG is compressed from near atmospheric pressure through a series of compressors. A higher pressure gas stream is produced which can be routed to uses for fuel or power within the LNG complex or may be routed to external users for fuel, power, or feedstock uses.

The integration opportunity of this embodiment comprises taking the BOG at an intermediate stage of compression, route it through the dehydroaromatization step and then utilize the remaining stages of BOG compression to achieve a disposition for the unreacted methane and the $H_2$ byproduct. Additional methane (additional to the BOG) containing feedstock may also be introduced to the reactor as well as $CO_2$, CO, $H_2O$, and/or $O_2$. The quantity of methane added should be sufficient to produce a quantity of off-gas for re-introduction to the BOG compression train such that the compressors are fully utilized.

One or more additional compression steps are necessary to provide the desired inlet pressure so that pre-existing compressors can still produce a sufficiently high pressure product stream to go to desired disposition. Benzene, toluene, and naphthalene (BTN) will be recovered from the stream using one or more steps to remove BTN as liquid products. Methods of recovery of BTN from such a stream are per se known, and include adsorption, absorption, condensation, membrane, and the like.

The recovery of BTN may also be located downstream of and/or integrate with compression steps. After BTN recovery, the stream would contain unreacted methane (illustrative: 66 mol %), $H_2$ byproduct (illustrative: 29 mol %), remainder ethylene byproduct, inerts ($N_2$, He, etc.), oxygen species (predominately CO) as well as contaminants (sulfur compounds, nitrogen compounds, metal compounds, etc.). A portion of the stream would be utilized to supply the lower pressure fuel and power needs associated with the aromatics production facilities. The remainder of the stream is routed to the preexisting BOG compression train. Minor modification (rotors, etc.) of these compressors may be helpful due to the lower density of the gas stream. One of ordinary skill in the art, in possession of the present disclosure, can accomplish this without more than routine engineering.

The compressed gas stream may be optionally routed to a purification device (e.g., membrane or adsorption) to produce a higher purity $H_2$ stream (or $H_2$ enriched stream) and a lower $H_2$ content stream, the latter of which may be routed to fuel or power within the LNG complex or advantageously routed to external users for fuel, power, or feedstock uses, such as feed for methanol synthesis or syngas generation. The $H_2$ enriched stream may be exported directly as a product or may be blended with regenerator off gas directed to a compressor; then to further purification (such as by membrane or adsorption) to produce a higher purity $H_2$ stream and a lower $H_2$ content stream (which may be recycled or routed to fuel disposition). The higher purity gas stream can be expanded for energy recovery, then routed to the catalyst regeneration reactor which takes catalyst with higher levels of coke from the dehydroaromatization reactor, removes a portion of the coke by reacting the coke with $H_2$ at elevated temperatures and pressures to produce methane; catalyst with reduced coke content is returned to the dehydroaromatization reactor.

The gas effluent from the regeneration reactor will have lower levels of $H_2$ and increased levels of methane, but may be purified for further use. One surprising result of this integration is that the inert content (e.g., $N_2$) of the BOG actually increases the conversion of methane for a given set of reaction conditions versus feeding pure methane. This provides yet a further advantage by allowing an opportunity to have higher pressure operation optimization of the dehydroaromatization reactor.

Accordingly, an embodiment of the invention concerns converting a gaseous stream comprising LNG BOG and/or Jetty BOG gas comprising methane to an aromatic hydrocarbon stream comprising at least one aromatic compound, said process comprising: (a) routing of gaseous stream LNG BOG and/or Jetty BOG gas to a reactor system and if required compressing said gaseous stream to a pressure sufficient to enter a reactor system; (b) passing said gaseous stream to one or more conversion zones containing at least one dehydroaromatization catalyst under conditions suitable for converting methane to $H_2$ and said at least one aromatic compound; (c) recovering said aromatic compounds thereby leaving a residual stream comprising gaseous methane and $H_2$. (d) Optional further comprising, compressing said residual methane and $H_2$ stream of (c) and routing said stream to a fuel disposition or other disposition. (e) Optional further comprising, recovering at least a portion of the $H_2$ as a $H_2$ rich stream from said stream of methane and $H_2$ after compression and prior to fuel disposition or other disposition.

One skilled in the art will recognize, once being made aware of the above information, that the above process integration would provide significant reduction in capital requirements and reduction in energy use.

In embodiments, the invention also concerns a process for dehydroaromatization and LNG regasification. In this embodiment, the cryogenic fractionation of the product stream of a dehydroaromatization reactor is cryogenically separated, the cryogenic separation combined with LNG regasification.

At locations remote from methane gas needs, methane containing feed gas is routed to one or more liquefaction facilities to produce LNG. The LNG is transported in multiple specialized ships to a location where the LNG is to be regasified for use. LNG cannot be utilized in the liquid form and must be converted back to a gas at high pressure for distribution to consumers. To supply vaporized gas at pipeline pressure, a portion of the gas is burned to provide heat, which is inefficient in that a portion of the gas is consumed. In this embodiment, the cryogenic value of LNG as a refrigerant is used to enable the cryogenic fractionation of methane and $H_2$ byproduct from dehydroaromatization at the same time eliminating the need or reducing the need to burn gas to regasify the LNG. Thus, the LNG is vaporized while simultaneously providing cryogenic refrigeration for the separation of $H_2$ from methane. The regasified methane is split into a methane product stream for use as fuel, power generation, or feedstock and feed which will be utilized for conversion to aromatics. Higher hydrocarbons (ethane, propane, etc.), inerts ($N_2$, He, etc.), oxygen containing co-feeds ($O_2$, $H_2O$, $CO_2$, CO) may also be blended with the feed to the dehydroaromatization step. In embodiments, this has potential advantages of one or more of the following: (1) providing the $H_2$ at a location where it has higher value, e.g., an industrialized location (2) an industrialized location may also have lower cost of construction than remote gas fields; (3) the opportunity for partial once through with the combined $H_2+CH_4$ going to low pressure fuel gas consumers thereby shrinking the entire separation section; e.g., a portion of the $H_2+CH_4$ stream is not separated but instead used as fuel, therefore with a reduced quantity stream of $H_2+CH_4$, the facilities to do $H_2/CH_4$ separation are smaller.

Accordingly, an embodiment of the invention concerns a process for converting an LNG stream comprising methane to a gaseous hydrocarbon stream comprising methane, an aromatic hydrocarbon stream comprising at least one aromatic compound, and a $H_2$ rich stream, said process comprising: (a) passing said LNG to a heating step where heat is supplied to gasify said LNG, wherein at least a portion of said heat is supplied from integration with the cryogenic separation of (f); (b) producing a gaseous hydrocarbon stream comprising methane and potentially higher hydrocarbon (e.g., ethane); (c) sending a first portion of the said gaseous hydrocarbon stream to one or more pipelines to convey said stream to one or more consumers of said stream as a fuel or feedstock; (d) sending a second portion of said gaseous stream to one or more conversion zones containing at least one dehydroaromatization catalyst under conditions suitable for converting methane to $H_2$ and said at least one aromatic compound; (e) recovering said aromatic compounds thereby leaving a residual stream comprising gaseous methane and $H_2$; (f) separating said methane and $H_2$ into a $H_2$ rich stream and a methane rich stream; wherein said separating is characterized by cryogenic separation wherein at least a portion of the refrigeration for said cryogenic separation is provided by integration with said gasification of LNG in (a); (g) routing said $H_2$ rich stream to a desired disposition with or without further processing; (h) routing said methane rich stream to fuel disposition or recycling said methane rich stream to said conversion zone of (d).

One skilled in the art will recognize, once being made aware of the above information, that the above process integration would provide significant reduction in capital requirements and at least some reduction in energy use.

The invention also concerns use of Associated Gas in a dehydroaromatization process. Quite often there is not a disposition for this gas and it is flared. In this embodiment, a gas that is rich in higher hydrocarbons (that is hydrocarbons of higher molecular weight than methane, such as ethane, propane, butane, etc.; e.g., typically gas associated with oil reserves) is processed by contact in dehydroaromatization zone with a dehydroaromatization catalyst under conditions suitable for conversion. Processing this gas through dehydroaromatization enables a portion of it to be upgraded to higher value product while at the same time reducing the total quantity of the gas stream and reducing the higher hydrocarbons so that a methane and $H_2$ rich stream is available for dispositions into which the higher hydrocarbon containing gas stream may not be suitable. The lower H/C ratio allows for higher thermodynamic conversion which can be an enabler for lower temperature and/or higher pressure operation and/or higher conversion at a given set of operating conditions. Essentially all of the higher hydrocarbons are converted to aromatics, methane and $H_2$. After aromatic recovery the residual gas could be processed by one or more of the following: (1) separated into $H_2$ and $CH_4$ (with $CH_4$ being recycled and/or used as fuel); (2) routed to liquefaction for $H_2$ recovery and production of LNG; (3) utilized to make syngas; (4) used for fuel or power. The first table (Table 1) below shows an example associated gas composition; the second table (Table 2) shows the yield vectors (by yield vectors we mean that change between feed and product, so that a negative value is disappearance <reaction> while a positive value is production; note that the vector is based on adjusting all species for their carbon content) for this feed at various temperatures and pressures; the third table (Table 3) provides the BT (Benzene+Toluene) yields, the gas yields, and the gas composition for this feed at various temperatures and pressures. Table 3 shows that it is possible to remove essentially all the heavy hydrocarbons from the feed and yield a product gas that will have low content of heavy hydrocarbons after the aromatics have been recovered from it.

TABLE 1

| Example associated gas composition | |
|---|---|
| Species | Mol % |
| C1H4 (Methane) | 34.46% |
| C2H6 (Ethane) | 19.87% |
| C3H8 (Propane) | 23.44% |
| C4H10 (Butanes) | 13.08% |

TABLE 1-continued

Example associated gas composition

| Species | Mol % |
|---|---|
| C5H12 (Pentanes) | 4.17% |
| C6H14 (Hexanes) | 2.27% |
| C7H18 (Heptanes) | 1.37% |
| CO2 | 1.16% |
| H2S | 0.00% |
| N2 | 0.18% |

TABLE 2

Product yield vectors; Carbon Yield Basis

| | T, ° C. | | | |
|---|---|---|---|---|
| | 800 | 750 | 800 | 800 |
| | | P, psia | | |
| | 20 | 20 | 35 | 50 |
| Species | C Yield | C Yield | C Yield | C Yield |
| METHANE | 34.86% | 38.01% | 37.03% | 38.19% |
| ETHANE | −16.32% | −16.31% | −16.28% | −16.25% |
| PROPANE | −29.05% | −29.05% | −29.05% | −29.05% |
| BUTANE | −21.61% | −21.61% | −21.61% | −21.61% |
| PENTANE | −8.61% | −8.61% | −8.61% | −8.61% |
| HEXANE | −5.63% | −5.63% | −5.63% | −5.63% |
| HEPTANE | −3.96% | −3.96% | −3.96% | −3.96% |
| CO2 | −0.48% | −0.48% | −0.48% | −0.48% |
| ETHENE | 0.39% | 0.25% | 0.37% | 0.35% |
| BENZENE | 47.14% | 44.02% | 44.42% | 42.84% |
| TOLUENE | 2.32% | 2.42% | 2.85% | 3.25% |
| CO | 0.96% | 0.96% | 0.96% | 0.96% |

TABLE 3

KTA
Feed Rate = 1,000 (kilotons/annum)

BT product rates and gas compositions

| T, ° C. | 800 | 750 | 800 | 800 |
|---|---|---|---|---|
| P, psia | 20 | 20 | 35 | 50 |
| KTA BT (Benzene + Toluene) | 495 | 464 | 473 | 461 |
| KTA Gas | 505 | 536 | 527 | 539 |
| Gas Composition (Mol %) | | | | |
| C1H4 | 73% | 80% | 78% | 81% |
| C2H6 + C2H4 | 0.3% | 0.2% | 0.3% | 0.3% |
| H2 | 25% | 18% | 20% | 18% |
| CO | 1.4% | 1.5% | 1.5% | 1.5% |

Accordingly, the present invention concerns a process for converting a gaseous feed stream comprising methane and higher hydrocarbons to a gaseous product stream comprising methane and a reduced quantity of higher hydrocarbons, and an aromatic hydrocarbon stream comprising at least one aromatic compound, said process comprising: (a) passing said gaseous stream to one or more conversion zones containing at least one dehydroaromatization catalyst under conditions suitable for converting methane to said at least one aromatic compound; (b) contacting said gaseous stream with said at least one catalyst so as to produce a product stream comprising at least one aromatic compound, $H_2$, and a gaseous hydrocarbon stream comprising methane and a reduced quantity of higher hydrocarbons other than aromatics; (c) recovering said aromatic compounds thereby leaving a residual stream comprising $H_2$, and comprising methane and a reduced quantity of higher hydrocarbons other than aromatics; (d) Optionally further comprising, compressing said residual stream of (c) and routing said stream to a fuel disposition; liquefaction to produce LNG, or other disposition. (e) Optionally further comprising, recovering at least a portion of the $H_2$ as a $H_2$ rich stream from said stream of methane and $H_2$ after compression and prior to fuel disposition or other disposition; (f) wherein said gaseous feed stream of (a) contains greater than 10 mol % of higher hydrocarbons and said gaseous product stream of (c) contains less than 5 mol % of higher non-aromatic hydrocarbons.

One skilled in the art will recognize, once being made aware of the above information, that the above process integration would provide significant reduction in capital requirements and at least some reduction in energy use.

A further understanding of the above can be obtained by reference to the specific embodiments provided by the figures. It will be understood that these are merely representative and that numerous other embodiments would be apparent to one of ordinary skill in the art in possession of the present disclosure. Furthermore it will be recognized that not all necessary apparatus are shown but would be readily apparent to the person ordinarily skill in the art, such as valves, control devices, and the like.

FIG. 1 is a schematic showing a novel process configuration for dehydroaromatization according to the invention, wherein methane is cryogenically separated from $H_2$ and the methane at least partially recycled back to the process, and furthermore wherein the $H_2$ used at least in part to regenerate the dehydroaromatization catalyst. It may be combined with processes for taking LNG from the well-head to consumer at numerous points, as will be pointed out at least in part in the following description. Addition points of combination will be pointed out with specificity elsewhere herein, and it will be understood that one of skill in the art, in possession of the present specification, would recognize numerous other opportunities.

In FIG. 1, line 117 is incoming (fresh) feed methane (for illustrative purposes being fed at 100 kg per hour nominal rate of methane feed); this stream may also contain higher hydrocarbons (ethane, propane, etc.), inerts ($N_2$, He, etc.), oxygen containing co-feeds ($O_2$, $H_2O$, $CO_2$, CO) as well as contaminants present in natural gas (sulfur compounds, nitrogen compounds, metal compounds, etc.). Line 118 is recycle methane (for illustrative purposes recycle rate would be ~240 kg/hr of recycle methane for 100 kg/hr nominal rate of fresh methane feed); recycle stream would also contain some residual $H_2$ and possible inerts and CO. 116 is the dehydroaromatization reactor containing a dehydroaromatization catalyst and operating at conditions sufficient to convert methane to benzene or other aromatic compounds (for illustrative purposes MoZSM-5 catalyst operated at 875° C. and 40 psia). The product of the dehydroaromatization reactor is passed to device 115, which may be a cyclone, wash column, filter, and the like, for removing most or all catalyst fines (which are removed in stream 119 from the product leaving the reactor). The product stream from 116 may be cooled before or after the fines are removed in the step denoted by 115, and then compressed in compressor 114. A stream 113 comprising BTN can be recovered by one or more steps 112. The "one or more steps" are desirably selected from steps comprising adsorption, absorption, condensation, membrane separation, and mixtures of two or more of these steps. The stream having BTN removed therefrom optionally may be further compressed in compressor 111 after BTN recovery. Stream 122 would contain unreacted methane (illustrative: 66 mol %), $H_2$ byproduct (illustrative: 29 mol %), ethylene byproduct, inerts ($N_2$, He, etc.), oxygen species (predominately CO) as well as contaminants (sulfur compounds, nitrogen compounds, metal compounds, etc.). 110 is the cryogenic fractionation to produce an $H_2$-depleted, methane-enriched stream for recycle 118 and a methane-depleted, $H_2$-enriched stream 109 for $H_2$ recovery. Stream 109 may be optionally routed to a purification device 107 (e.g., membrane separation or adsorption device) to produce a higher purity $H_2$ stream 106 and a lower $H_2$ content stream 108 which may be routed to fuel use or other dispositions such as feed for methanol synthesis or syngas generation. The $H_2$ enriched stream may be exported directly as a product or may be directed to a catalyst regeneration reactor 105 which takes catalyst with higher levels of coke 121 from the dehydroaromatization reactor 116, removes a portion of the coke by reacting the coke with $H_2$ at elevated temperatures and pressures in 105 to produce methane; and catalyst with reduced coke content 120 is returned to the dehydroaromatization reactor 116. The gas effluent 103 from the regeneration reactor 105 will have lower levels of $H_2$ and increased levels of methane, but is still a very good feed for certain processes, such as methanol synthesis. $CO_2$ and/or CO (stream 101) may be blended with the $H_2$ containing stream 103 and compressed in compressor 102 to produce a feed stream 104 for methanol synthesis (by way of example; process not shown but known per se). It has been surprisingly discovered that in embodiments it is advantageous to blend the $CO_x$ (x is 1 and/or 2) with the $H_2$-containing stream prior to compression to increase the gas density and reduce compression investment.

Note that heat exchangers (heating and cooling), valves, furnaces, and the like, are not shown on these simplified process flow diagrams but would be readily apparent to one of skill in the art in possession of the present disclosure.

Figure 2:
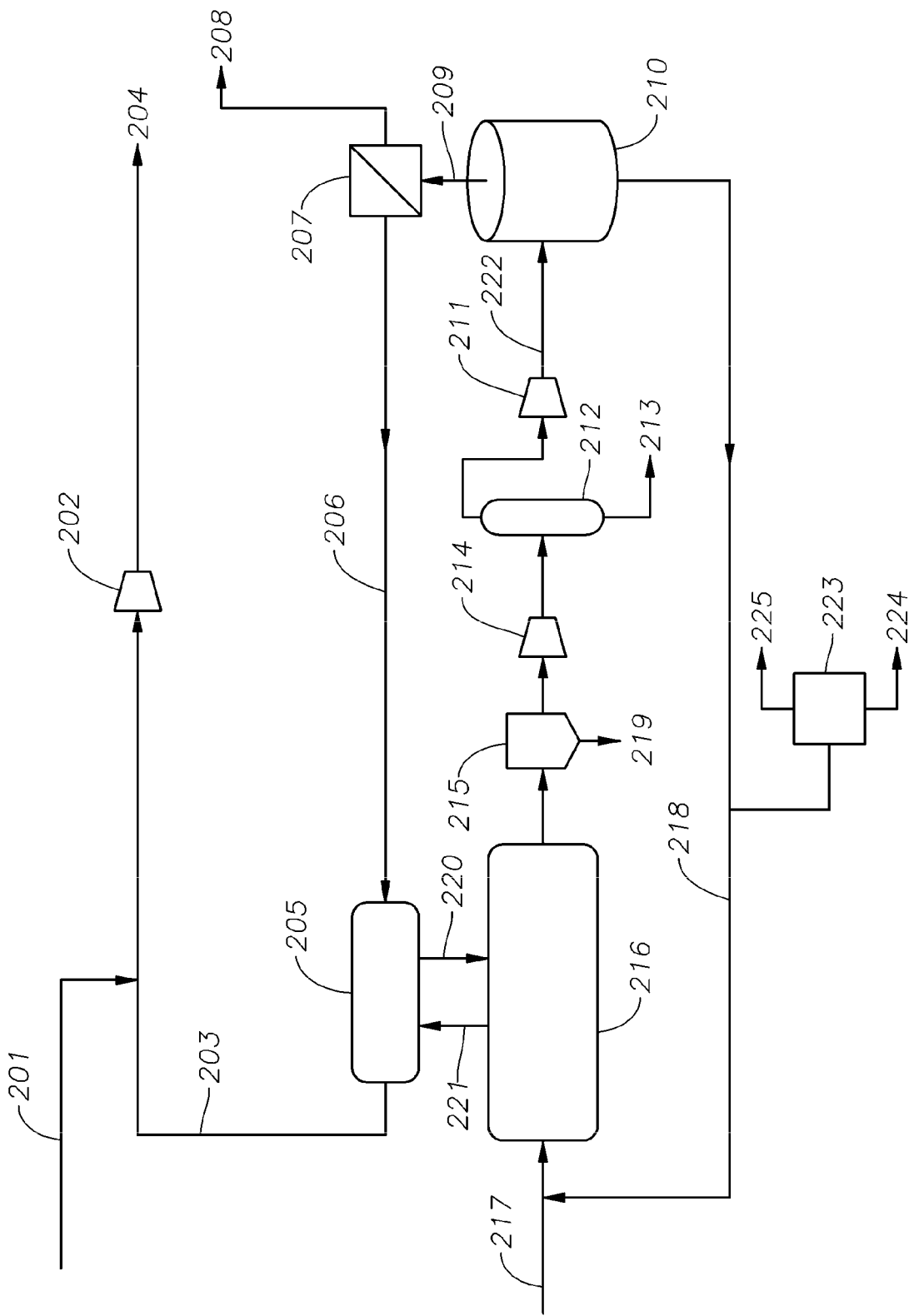
FIG. 2 illustrates an embodiment of the invention wherein the dehydroaromatization process is integrated with a flashing step used to separate an LNG stream into LNG BOG and a final LNG product stream.

FIG. 2 illustrates an embodiment of the invention wherein the dehydroaromatization process is integrated with the production of LNG; a flashing step is used to separate a stream into LNG BOG and a final LNG product stream.

In FIG. 2, line 217 is incoming (fresh) feed methane (for illustrative purposes being fed at 340 kg per hour nominal rate of methane feed); this stream may also contain higher hydrocarbons (ethane, propane, etc.), inerts ($N_2$, He, etc.), oxygen containing co-feeds ($O_2$, $H_2O$, $CO_2$, CO) as well as contaminants present in natural gas (sulfur compounds, nitrogen compounds, metal compounds, etc.). 216 is the dehydroaromatization reactor containing a dehydroaromatization catalyst and operating at conditions sufficient to convert methane to benzene or other aromatic compounds (for illustrative purposes MoZSM-5 catalyst operated at 875 C and 40 psia). 215 is a device (cyclone, wash column, filter, etc.) for removing most or all catalyst fines, removed through 219 from the product leaving the reactor and proceeding to compressor 214. And again, cooling may be done before and/or after this device 215. After fines removal and cooling, the stream is compressed in compressor 214. BTN (stream 213) is recovered from the stream using one or more steps conveniently illustrated schematically by device 212 to remove BTN as liquid products. Again, as in FIG. 1, possible means of recovery include at least one of adsorption, absorption, condensation, membrane. Further compression 211 may be done after BTN recovery. Stream 222 would contain unreacted methane (illustrative: 66 mol %), $H_2$ byproduct (illustrative: 29 mol %), ethylene byproduct, inerts ($N_2$, He, etc.), oxygen species (predominately CO) as well as contaminants (sulfur compounds, nitrogen compounds, metal compounds, etc.). 210 is the cryogenic fractionation to produce an $H_2$ depleted, methane enriched stream 218 and a methane depleted, $H_2$ enriched stream 209 for $H_2$ recovery. A portion of stream 218 may be recycled to the dehydroaromatization reactor 216 and a portion or all of stream 218 may be routed to a flash drum 223 where a portion of the material is flashed off at near atmospheric pressure to remove $H_2$, CO and $N_2$ (line 225) which can be routed to fuel use or other disposition and a remaining product liquefied methane, stream 224 (for illustrative purposes the rate would be ~240 kg/hr of product LNG for 340 kg/hr nominal rate of fresh methane feed).

Stream 209 may be optionally routed to a purification device 207 (e.g., membrane or adsorption) to produce a higher purity $H_2$ stream 206 and a lower $H_2$ content stream 208 which may be routed to fuel use or other dispositions such as feed for methanol synthesis or syngas generation. The $H_2$ enriched stream may be exported directly as a product or may be directed to a catalyst regeneration reactor 205 which takes catalyst with higher levels of coke 221 from the dehydroaromatization reactor 216, removes a portion of the coke by reacting the coke with $H_2$ at elevated temperatures and pressures in 205 to produce methane; catalyst with reduced coke content 220 is returned to the dehydroaromatization reactor 216. The gas effluent 203 from the regeneration reactor 205 will have lower levels of $H_2$ and increased levels of methane, but is still a very good feed for certain processes, such as methanol synthesis. $CO_2$ and/or CO (stream 201) may be blended with the $H_2$ containing stream 203 and compressed 202 to produce a feed stream 204 for methanol synthesis (by way of example). Again, as in the previous embodiment, it was surprisingly discovered to be advantageous to blend the $CO_x$ (x=1 and/or 2) with the $H_2$ containing stream prior to compression to increase the gas density and reduce compression investment.

Figure 3:
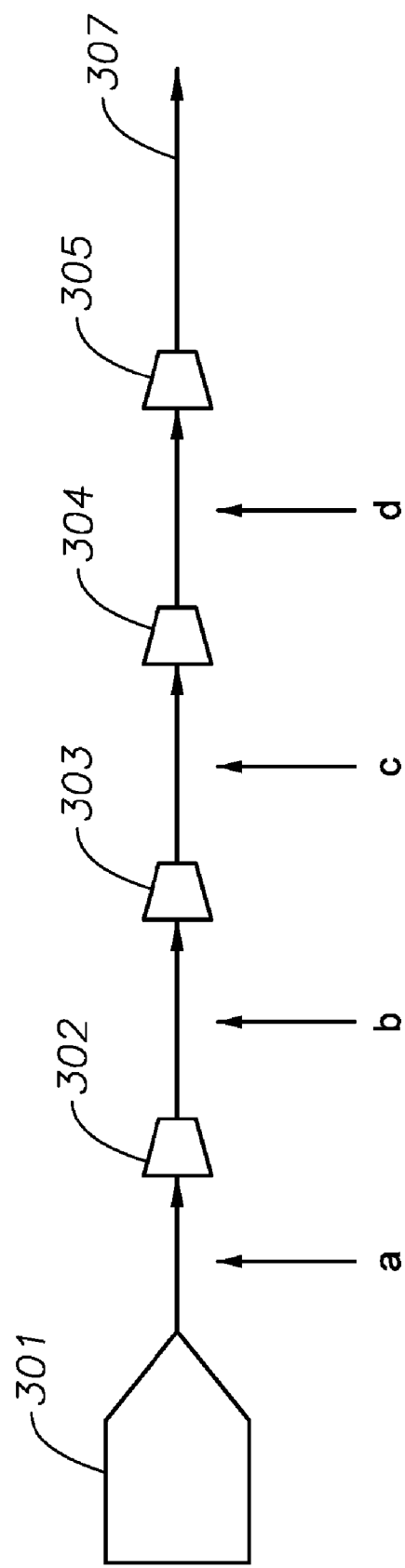
FIG. 3 shows base case compression of BOG streams generated in LNG or ship loading operations.

FIG. 3 illustrates an embodiment of the invention, showing base case compression of BOG streams generated in LNG or ship loading operations.

With regard to FIG. 3, in LNG operations low pressure, near atmospheric pressure streams are generated. These may be for instance LNG train boil off gas (LNG BOG) or loading jetty boil off gas (Jetty BOG). LNG BOG is produced when, after the final stage of heat exchange, the refrigerated stream is flashed down to near atmospheric pressure to produce a near atmospheric pressure liquid stream of LNG product and the LNG BOG. Jetty BOG is produced when LNG is in storage tanks and some liquid is converted to vapor by heat incursion into the tank or when LNG is loaded into stationary or on-ship tanks and vapor is created due to displacement of inert blanket that is previously in the tank as well as by vaporization caused if the tank is at a temperature greater than the LNG. BOG typically contains 85 to 95 mol % methane and 10 to 15 mol % nitrogen. Stream 301 is LNG BOG, Jetty BOG, or a combination of the two. The gas is compressed from near atmospheric pressure through a series of compressors; four are shown here (units 302, 303, 304, and 305) but more or fewer may be required depending on the compressor type and the ultimate pressure increase desired. A higher pressure gas stream is produced 307 which can be routed to uses for fuel or power within the LNG complex or may be routed to external users for fuel, power, or feedstock uses. In embodiments, integration of this BOG stream with a dehydroaromatization process may occur at any one or more of lines a, b, c, and d. An example of this is shown in the embodiment illustrated in FIG. 4.

Figure 4:
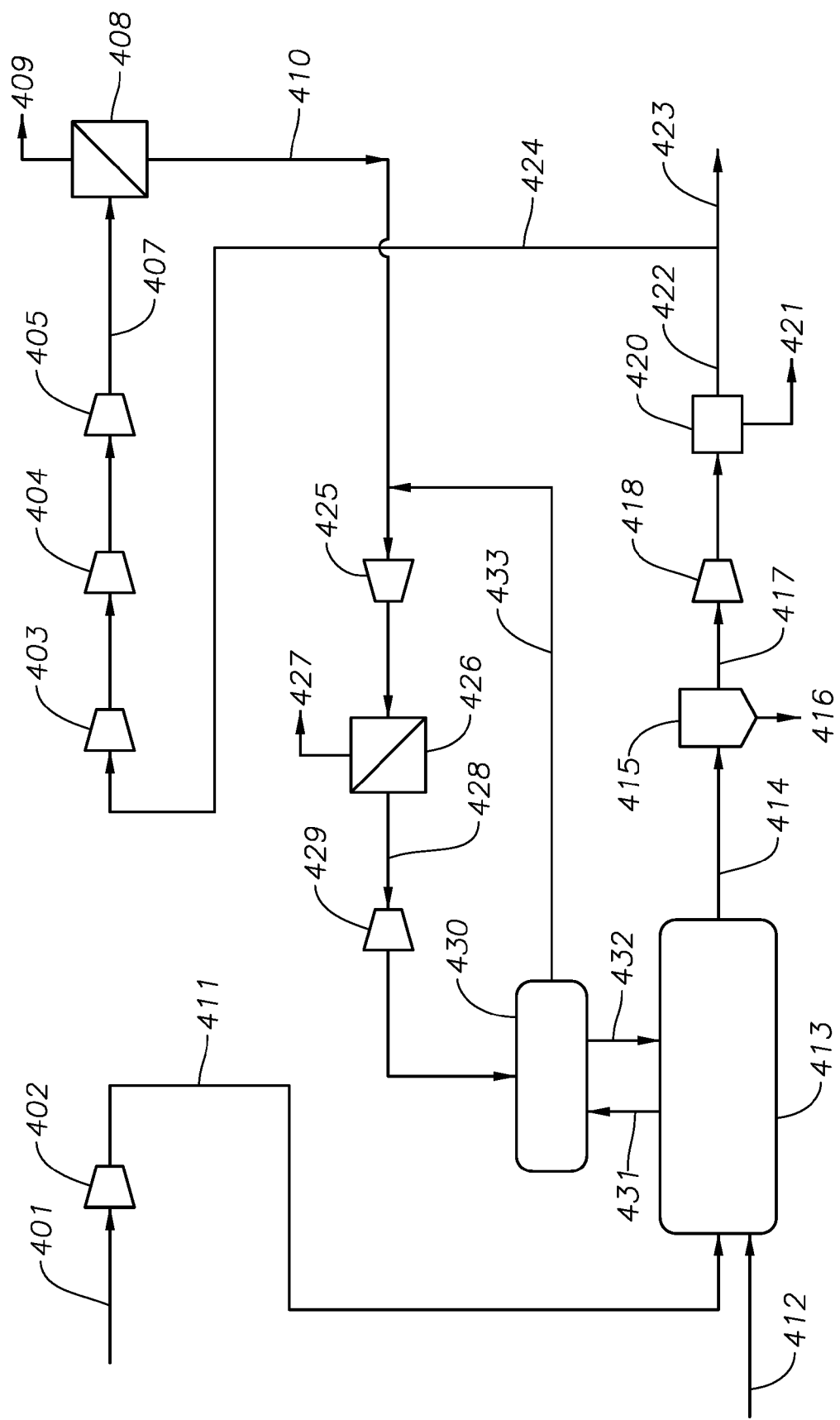
FIG. 4 illustrates schematically a combination of a retrofit and integration of the compressors used in a system according to the invention, such as FIG. 3.

FIG. 4 illustrates yet another embodiment of the invention: Note that this schematic illustrates a situation that may be considered, in embodiments, a retrofit and integration of the compressors shown in FIG. 3. That is, compressors 402, 403, 404, and 405 in FIG. 4 may correspond to the compressors 302 through 305 in FIG. 3. Thus, this embodiment may use pre-existing equipment with a pre-existing disposition for the gas product stream (e.g., 307 as detailed on FIG. 3) and provide for low cost modifications. Stream 401 is LNG BOG, Jetty BOG, or a combination of the two. The gas is partially compressed through one or more compressors 402 to produce a stream 411 which is at sufficient pressure to enter the reactor system 413. Additional methane containing feedstock 412 may also be introduced to the reactor as well as $CO_2$, CO, $H_2O$, and/or $O_2$. In a preferred embodiment, the quantity of methane added via stream 412 advantageously should be sufficient to ultimately produce a quantity of gas stream 424 such that the compressors 403, 404, and 405 are fully utilized. 413 is the dehydroaromatization reactor containing a dehydroaromatization catalyst and operating at conditions sufficient to convert a portion of the methane to benzene or other aromatic compounds (stream 414) (for illustrative purposes MoZSM-5 catalyst operated at 875° C. and 40 psia). 415 is a device (such as a cyclone, wash column, filter, etc.) for removing most or all catalyst fines (stream 416) from the product leaving the reactor; cooling may be done before and/or after this device, producing a stream 417 substantially free of solids. After fines removal, compression 418 and cooling (not shown) will be done to the stream. The order (cooling/compression) may be optimally determined by one of ordinary skill in the art. Compression step 418 is preferably optimized to provide the desired inlet pressure so that pre-existing compressors 403, 404, and 405 can still produce a sufficiently high pressure product stream 409 to go to selected disposition. BTN (stream 421 will be recovered from the stream using one or more steps 420 to remove BTN as liquid products (similar to what was discussed previously with respect to element 113 in FIG. 1). As discussed previously, recovery steps are preferably selected from steps of adsorption, absorption, condensation, membrane, and combinations thereof. Note that the recovery of BTN (unit 420) may also be located downstream of and/or integrate with compression steps 403, 404, and 405. Stream 422 contains unreacted methane (illustrative: 66 mol %), $H_2$ byproduct (illustrative: 29 mol %), ethylene byproduct, inerts ($N_2$, He, etc.), oxygen species (predominately CO) as well as contaminants (sulfur compounds, nitrogen compounds, metal compounds, etc.). An optional stream 423 could be utilized to supply the lower pressure fuel and power needs associated with the aromatics production facilities. All or the remainder of the stream 424 is routed to the preexisting compression train, shown here as three compressors 403, 404, and 405. Minor modification (rotors, etc.) of these compressors may be helpful due to the lower density of the gas stream. The compressed gas stream 407 may be optionally routed to a purification device 408 (e.g., membrane or adsorption) to produce a higher purity $H_2$ stream 410 and a lower $H_2$ content stream 409 which may be routed to fuel or power within the LNG complex or may be routed to external users for fuel, power, or feedstock uses dispositions such as feed for methanol synthesis or syngas generation.

The $H_2$ enriched stream 410 may be exported directly as a product (path not shown) or may be blended with regenerator off gas (stream 433 from element 430, discussed in more detail below) and directed to a compressor 425; then to further purification 426 such as by membrane separation or one or more adsorption processes to produce a higher purity $H_2$ stream 428 and a lower $H_2$ content stream 427 which may be recycled to unit 408 (the necessary path for which is not shown, for convenience of view) or routed to fuel disposition (not shown). The higher purity gas stream 428 is then optionally expanded (unit 429) for energy recovery, then used in the catalyst regeneration reactor 430 which takes catalyst with higher levels of coke 431 from the dehydroaromatization reactor 413, removes a portion of the coke by reacting the coke with $H_2$ at elevated temperatures and pressures in 430 to produce methane; catalyst with reduced coke content 432 is returned to the dehydroaromatization reactor 413. The gas effluent 433 from the regeneration reactor 430 (which mixes with stream 410) will have lower levels of $H_2$ and increased levels of methane, but may be purified for further use.

Figure 5:
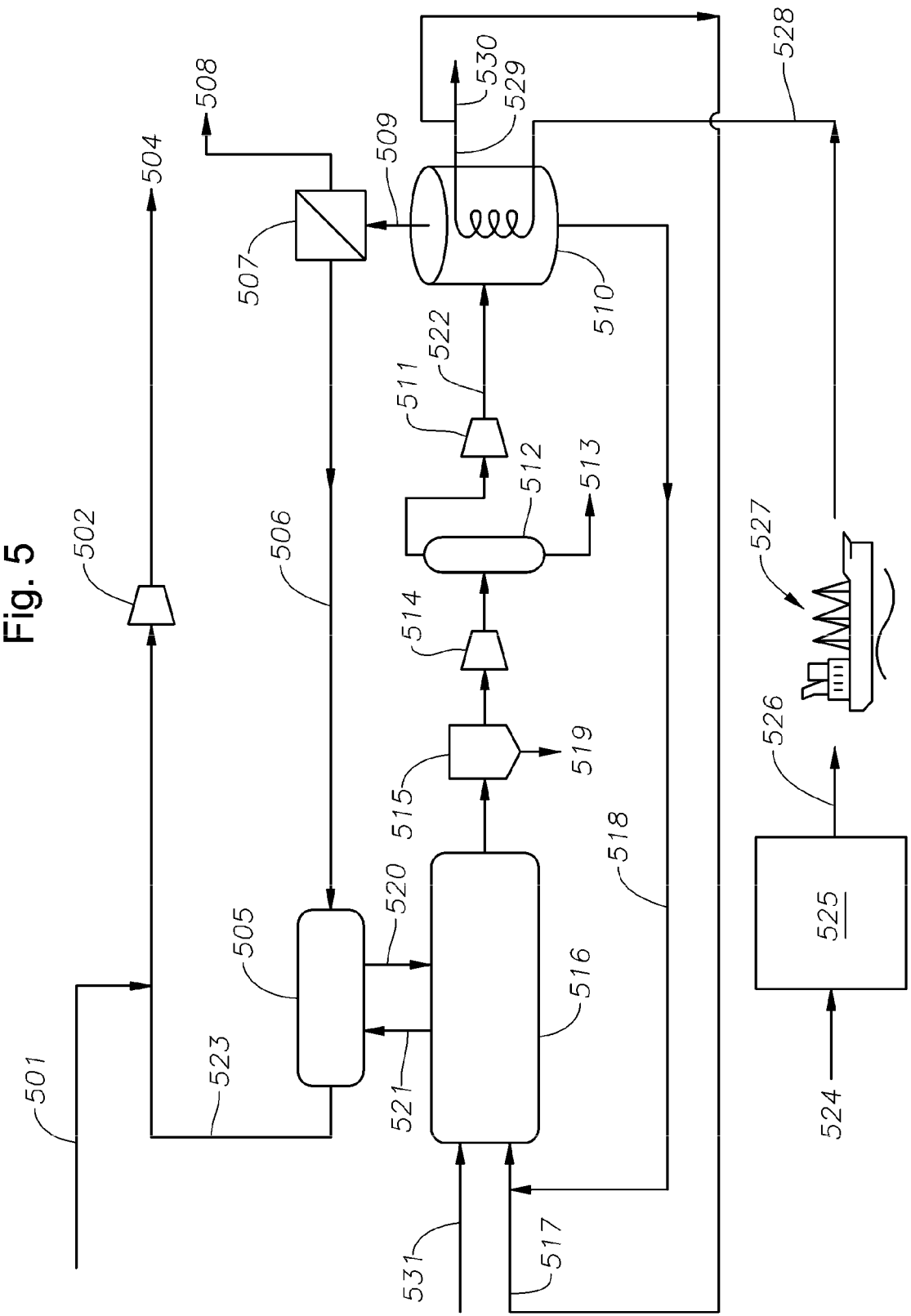
FIG. 5 illustrates the integration of LNG processing with aromatics production from methane wherein the regasification of LNG is used to provide refrigeration for the separation of methane and $H_2$.

FIG. 5 illustrates still another embodiment of the invention, and shows the integration of LNG processing with aromatics production from methane wherein the regasification of LNG is used in the separation of methane and $H_2$.

As shown in FIG. 5, at a location remote from methane gas needs, a methane containing feed gas stream 524, is routed to one or more liquefaction facilities 525 to produce LNG (stream 526). (Note that the various steps illustrated by 524 through 526 may themselves be integrated with dehydroaromatization according to the present invention, e.g., with regard to BOG generated in these steps, however in the present illustration we will assume steps 524-526 occur in a remote location not having the necessary integration infrastructure and, after transportation by, e.g., ship, the remaining steps occur in an industrialized location). The LNG is transported in multiple specialized ships 527. At a location where the LNG is to be regasified for use it is routed (stream 528) to unit 510 where the LNG is vaporized while simultaneously providing cryogenic refrigeration for the separation of $H_2$ from methane. The regasified methane stream 529 is split into a methane product stream 530 for use as fuel, power generation, or feedstock and stream 517 (for illustrative purposes being fed at 100 kg per hour nominal rate of methane) which will be utilized for conversion to aromatics. Stream 531 (which may contain higher hydrocarbons ethane, propane, etc.), inerts ($N_2$, He, etc.), oxygen containing co-feeds ($O_2$, $H_2O$, $CO_2$, CO) may also be blended with stream 517. Line 518 is recycled methane (for illustrative purposes recycle rate would be ~240 kg/hr of recycle methane for 100 kg/hr nominal rate of fresh methane feed); recycle stream would also contain some residual $H_2$ and possible inerts and CO. Apparatus 516 is the dehydroaromatization reactor containing a dehydroaromatization catalyst and operating at conditions sufficient to convert methane to benzene or other aromatic compounds (for illustrative purposes MoZSM-5 catalyst operated at 875° C. and 40 psia). 515 is a device (such as a cyclone, wash column, filter, etc.) for removing most or all catalyst fines (stream 519) from the product leaving the reactor 516. Cooling may be done before and/or after this device 515. After fines removal cooling and compression 514 BTN (stream 513) will be recovered from the stream using one or more steps 512 to remove BTN as liquid products. As in other embodiments discussed elsewhere herein, possible steps of recovery include one or more of adsorption, absorption, condensation, and membrane separation. Further compression 511 may optionally be done after BTN recovery. Stream 522 contains unreacted methane (illustrative: 66 mol %), $H_2$ byproduct (illustrative: 29 mol %), ethylene byproduct, inerts ($N_2$, He, etc.), oxygen species (predominately CO) as well as contaminants (sulfur compounds, nitrogen compounds, metal compounds, etc.). Cryogenic fractionation at device 510 is performed to produce an $H_2$ depleted, methane enriched stream for recycle 518 and a methane depleted, $H_2$ enriched stream 509 for $H_2$ recovery. Stream 509 may be optionally routed to a purification device 507 (e.g., membrane or adsorption) to produce a higher purity $H_2$ stream 506 and a lower $H_2$ content stream 508 which may be routed to fuel use or other dispositions such as feed for methanol synthesis or syngas generation. The $H_2$ enriched stream may be exported directly as a product or may be directed to a catalyst regeneration reactor 505 which takes catalyst with higher levels of coke 521 from the dehydroaromatization reactor 516, removes a portion of the coke by reacting the coke with $H_2$ at elevated temperatures and pressures in 505 to produce methane; catalyst with reduced coke content 520 is returned to the dehydroaromatization reactor 516. The gas effluent 523 from the regeneration reactor 505 will have lower levels of $H_2$ and increased levels of methane, but is still a very good feed for certain other processes such as methanol synthesis. $CO_2$ and/or CO (stream 501) may be blended with the $H_2$ containing stream 523 and compressed 502 produce a feed stream 504 for methanol synthesis (by way of example); it was discovered to be advantageous to blend the $CO_x$ with the $H_2$ containing stream prior to compression to increase the gas density and reduce compression investment.

Feedstock

Any methane-containing feedstock can be used in the present process but in general the process is intended for use with a natural gas feedstock which includes gas co-produced with oil. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can be converted directly to aromatics products in the dehydroaromatization step. In addition, as will be discussed below, carbon dioxide can be converted to useful aromatics products indirectly through conversion to methane and/or ethane in a $H_2$ rejection step.

Nitrogen and/or sulfur impurities are also typically present in methane-containing streams and desirably are removed, or reduced to low levels, prior to use of the streams in the process of the invention. In an embodiment, the feed to the dehydroaromatization step contains less than 100 ppm, for example less than 10 ppm, such as less than 1 ppm each of nitrogen and sulfur compounds.

In addition, the feed to the dehydroaromatization step may contain at least one of $H_2$, water, oxygen, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydroaromatization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydroaromatization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydroaromatization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydroaromatization step contains $H_2$ and comprises about 80 to about 99.9 mol %, such as about 95 to about 99 mol %, methane and about 0.1 to about 20 mol %, such as about 1 to about 5 mol %, $H_2$.

The feed to the dehydroaromatization step can also contain higher hydrocarbons than methane, including aromatic hydrocarbons. Such higher hydrocarbons can be recycled from a $H_2$ rejection step, added as separate co-feeds or can be present in the methane stream, such as, for example, when ethane is present in a natural gas feed. Higher hydrocarbons recycled from a $H_2$ rejection step typically include one-ring aromatics and/or paraffins and olefins having predominately 6 or less, such as 5 or less, for example 4 or less, typically 3 or less carbon atoms. In some embodiments, the feed to the dehydroaromatization step contains less than 5 wt %, such as less than 3 wt %, of $C_3$+hydrocarbons.

Dehydroaromatization Catalyst

Any dehydroaromatization catalyst effective to convert methane to aromatics can be used in the present process, although generally the catalyst will include a metal component, particularly a transition metal or compound thereof, on an inorganic support. In many cases the support may modify the catalytic behavior of the metal component or may even have some catalytic activity of its own. Preferably, the metal component is present in an amount between 0.1% and 20%, or between 1% and 10%, by weight of the total catalyst.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth, and transuranium metals. Such metal components may be present in elemental form or as metal compounds, such as oxides, carbides, nitrides, sulfides and/or phosphides, and may be employed alone or in combination. Platinum and osmium can also be used as one of the metal component but, in general, are not preferred The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates, or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49, and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y, and dealuminized Y), LTL (e.g., zeolite L), IWW (e.g., ITQ-22), VFI (e.g., VPI-5), AEL (e.g., SAPO-11), AFI (e.g., ALPO-5), and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34, and SAPO-35. Suitable mesoporous materials include MCM-41, MCM-48, MCM-50, and SBA-15.

Examples of preferred catalysts include molybdenum, tungsten, zinc, rhenium, and compounds and combinations thereof on ZSM-5, silica, or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion, and physical mixing. In addition, the inorganic support can be modified by known methods, such as, for example, steaming, acid washing, caustic washing, and/or treatment with silicon-containing compounds, phosphorus-containing compounds, and/or elements or compounds of Groups 1, 2, 3, and 13 of the Periodic Table of the Elements. Such modifications can be used to alter the surface activity of the support and hinder or enhance access to any internal pore structure of the support.

The catalyst may also include a binder to provide the catalyst particles with the requisite size, density and hardness for use in the dehydroaromatization process. Suitable binders include refractory inorganic oxides such as alumina, silica, amorphous silica-alumina, zirconia, titanium oxide, and boron oxide. The catalyst may also contain fillers to adjust physical properties such as density and heat capacity. Preferred fillers are low surface area, low activity materials with SiC being preferred.

The following are representative examples of preferred catalyst preparations and should not be taken as limiting of the present invention.

EXAMPLE 1

A Mo/ZSM-5 material was prepared for use in preparing bound catalyst particles. 1000 g of a commercially manufactured ZSM-5 having a silica to alumina mole ratio of 25:1 and a crystal size of about 0.5 micron was blended with 113.28 g of $MoO_3$ (Aldrich, 99.5%) for 2 hours in two batches. The batches were combined and calcined in a muffle furnace with flowing air for five hours at 500° C. with a heat-up ramp rate of 1° C./minute. The resulting Mo level was measured to be 6.7 wt % via XRF analysis.

EXAMPLE 2

The material of Example 1 was used to prepare a 65 wt % MoZSM-5/35 wt % titania catalyst particle. 68.4 grams of the Mo/ZSM-5 were mulled with 35.9 g of titania (Degussa P-25) for 10 minutes. Water was added to produce a 65.7% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.5 wt % via XRF analysis.

EXAMPLE 4

The material of Example 1 was used to prepare a 65 wt % MoZSM-5/35 wt % alumina catalyst particle. 68.4 grams of the Mo/ZSM-5 were mulled with 38.6 g of alumina (UOP Versal 300) for 10 minutes. Water was added to produce a 53.8% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.0 wt % via XRF analysis.

EXAMPLE 6

The material of Example 1 was used to prepare a 65 wt % MoZSM-5/35 wt % silica catalyst particle. 64.8 grams of the Mo/ZSM-5 were mulled with 43.8 g of silica (Grace Davison Ludox HS-40), 19.2 g of silica (Degussa, UltraSil VN3-SP) and 1.96 g of caustic solution at 10 minute intervals. Water was added to produce a 75.2% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.6 wt % via XRF analysis.

EXAMPLE 9

The material of Example 1 was used to prepare a 80 wt % MoZSM-5/20 wt % zirconia catalyst particle. 84.2 grams of the Mo/ZSM-5 were mulled with 20 g of zirconium (IV) oxide (Aldrich, 99%) for 10 minutes. Water was added to produce a 63.8% solids mix. The material was extruded to 1/10" cylinder extrudate. The extrudate was dried and calcined in a muffle for 6 hours at 1000° F. (540° C.) in flowing air with a heat up rate of 5° F. (3° C.)/minute. The resulting Mo level was measured to be 5.2 wt % via XRF analysis.

EXAMPLE 10

The material of Example 1 was used to prepare a 65 wt % MoZSM-5/15% silicon carbide/20 wt % silica catalyst particle. 69.3 grams of the Mo/ZSM-5 were mulled with 25 g of silica (Grace Davison Ludox HS-40), 11 g of silica (Degussa, UltraSil VN3-SP) and 15 g of silicon carbide (Aldrich) at 10 minute intervals. Water was added to produce a 65% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.7 wt % via XRF analysis.

EXAMPLE 11

The material of Example 1 was used to prepare a 65 wt % MoZSM-5/15% silicon carbide/20 wt % titania catalyst particle. 44.68 grams of the Mo/ZSM-5 were mulled with 13.44 g of titania (Degussa, P-25) and 9.9 g of silicon carbide (Aldrich) at 10 minute intervals. Water was added to produce a 65.7% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.8 wt % via XRF analysis.

Dehydroaromatization Process

In the dehydroaromatization step of the present process, the methane containing feedstock is contacted with the particulate dehydroaromatization catalyst under conditions, normally non-oxidizing conditions and typically reducing conditions, effective to convert the methane to higher hydrocarbons, including benzene and naphthalene. The principal net reactions involved are as follows:

$$2CH_4 \leftrightarrow C_2H_4 + 2H_2 \qquad \text{(Reaction 1)}$$

$$6CH_4 \leftrightarrow C_6H_6 + 9H_2 \qquad \text{(Reaction 2)}$$

$$10CH_4 \leftrightarrow C_{10}H_8 + 16H_2 \qquad \text{(Reaction 3)}$$

Carbon dioxide that may be present in the feed improves catalyst activity and stability but negatively impacts equilibrium by allowing competing net reactions, such as;

$$CO_2 + CH_4 \leftrightarrow 2CO + 2H_2 \qquad \text{(Reaction 4).}$$

The dehydroaromatization step is conducted by contacting the methane-containing feedstock with the particulate dehydroaromatization catalyst in one or more fixed bed, moving bed or fluidized bed reaction zones. Generally, the feedstock is contacted in the reaction zone, or reaction zones in the case of multiple zones, with a moving bed of dehydroaromatization catalyst, wherein the feedstock flows countercurrent to the direction of movement of the dehydroaromatization catalyst. In one embodiment, the (or each) reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the dehydroaromatization reaction is conducted in a plurality of series-connected fluidized bed reactors in which particulate catalyst is cascaded in one direction from one reactor to the next adjacent reactor in the series, while the feed is passed through and between the reactors in the opposite direction.

In some embodiments, a non-catalytic particulate material may be supplied to the dehydroaromatization reaction zone(s) in addition to the catalytic particulate material. The non-catalytic particulate material may be used as a material to transport energy (heat) into the system and/or to fill space, as required, and providing the desired hydrodynamic environment. The non-catalytic particulate material may form particulates without a binder or may be bound with an inorganic binder such as clay, silica, alumina, zirconia, or other metal oxide used to help maintain the physical integrity of the particles. Preferably the particles are of a substantially spherical shape. Examples of suitable non-catalytic particulate material are low surface area silica, alumina, ceramics, and silicon carbide. By low surface area, we mean materials with surface areas of <50 meters$^2$/gram; preferably <25 meters$^2$/gram; more preferably <10 meters$^2$/gram; most preferably <5 meters$^2$/gram or even <1 meters$^2$/gram.

Typically, the mass ratio of the flow rate of the catalytic particulate material plus any non-catalytic particulate material over the flow rate of the hydrocarbon feedstock in the or each dehydroaromatization reaction zone is from about 1:1 to about 100:1, such as from about 1:1 to about 40:1, preferably from about 5:1 to 20:1.

The dehydroaromatization reaction is endothermic and hence the temperature in each dehydroaromatization reaction zone will tend to decrease from a maximum temperature to a minimum temperature as the reaction proceeds. Suitable conditions for the dehydroaromatization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydroaromatization reaction to reduce the temperature drop during the reaction and hence in some configurations it is possible to reduce the difference between the maximum and minimum temperatures to essentially zero. Alternatively, by supplying heated catalyst to the dehydroaromatization reaction, it is possible to produce an inverse temperature profile; that is with the process gas outlet reaction temperature being greater than the process gas inlet reaction temperature.

In one embodiment, the countercurrent flow of the feedstock and the particulate dehydroaromatization catalyst is arranged to produce an inverse temperature profile across dehydroaromatization reaction system, such that, despite the endothermic nature of the dehydroaromatization reaction, the difference between the reaction temperature of the gaseous effluent at the gas stream outlet from the dehydroaromatization reaction system and the reaction temperature of the methane-containing feed at the gas stream inlet to the dehydroaromatization reaction system is at least +10° C., such as at least +50° C., for example at least +100° C., and even at least +150° C.

In any event, since the dehydroaromatization reaction is endothermic, the catalytic particulate material enters the dehydroaromatization reaction system at a first, high temperature, typically about 800° C. to about 1200° C., such as about 900° C. to about 1100° C., and exits the reaction system at a second lower temperature, typically about 500° C. to about 800° C., such as about 600° C. to about 700° C. In preferred embodiments, the total temperature difference of the catalytic particulate material across the reaction zones is at least 100° C.

Other conditions used in the dehydroaromatization reaction generally include a pressure of about 1 kPa to about 1000 kPa, such as about 10 to about 500 kPa, for example about 50 kPa to about 200 kPa and a weight hourly space velocity of about 0.01 to about 1000 hr$^{-1}$, such as about 0.1 to about 500 hr$^{-1}$, preferably 1 to 20 hr$^{-1}$. In some embodiments, the dehydroaromatization step is conducted in the absence of $O_2$.

The major components of the effluent from the dehydroaromatization step are $H_2$, benzene, toluene, naphthalene, carbon monoxide, ethylene, and unreacted methane. Typically, the effluent contains at least 5 wt %, such as at least 10 wt %, for example at least 20 wt %, conveniently at least 30 wt %, more aromatic rings than the feed.

The benzene and naphthalene are separated from the dehydroaromatization effluent, for example, by solvent extraction followed by fractionation, and can be recovered as a product stream. However, at least part of these aromatic components can be submitted to an alkylation step, before or after product recovery, to produce higher value materials, such as xylenes. Moreover, the present process utilizes the $H_2$ generated as a by-product of the dehydroaromatization reaction and in particular converts at least part of the $H_2$ to higher value products.

Details of catalyst and reactors useful in the present invention may be found by reference to U.S. Patent Publications 2008/0047872; 2008/0058564; 2007/0249740; 2007/0129587 (now allowed); 2007/0282145; 2008/0021251; 2008/0051617; 2007/0249880; 2007/0260098; 2009/0030253; U.S. Pat. Nos. 7,589,246 and 7,659,437; WO 2009/097067, WO 2009/033198; and WO 2007/123808.

Details of additional steps, such as catalyst reheating, catalyst regeneration, catalyst reactivation, and catalyst recarburizing, and other aspects such as hydrogen management, aromatic product recovery and downstream management of the aromatic product, are not per se the subject of the present invention, except as otherwise noted herein, and reference may be made to common knowledge in the art, such as represented by prior art publications cited hereinabove.

Product Differentiation

It will be appreciated that aromatic hydrocarbons, like all hydrocarbons, inherently contain deuterium and $^{13}C$ in amounts that can vary according to the source of the carbon and hydrogen atoms in the molecule. In particular, studies of isotope distributions have shown that the amounts of deuterium and $^{13}C$ in naturally-occurring geologic methane are significantly different from the amounts of deuterium and $^{13}C$ in naphtha and that the amount of $^{13}C$ in naturally-occurring geologic $CO_2$ is significantly different from the amounts of $^{13}C$ in naturally-occurring geologic methane and in naphtha. Thus, analysis of the distribution of deuterium and $^{13}C$, can be used to differentiate between aromatic hydrocarbons produced using the present dehydroaromatization process and aromatic hydrocarbons produced from naphtha.

Thus, for example, if the measure of isotope abundance for deuterium in a benzene or xylene sample is defined as:

$$\delta(\text{deuterium}) = (R'_{sample}/R'_{standard} - 1) \times 1000$$

where $R'_{sample}$ is the ratio of deuterium to hydrogen in the benzene or xylene; and $R'_{standard}$ is the ratio of the natural abundance of deuterium to the natural abundance of hydrogen (which is equal to 0.00015/0.99985); and the measure of isotope abundance for $^{13}C$ in the sample is defined as:

$$\delta(^{13}C) = (R''_{sample}/R''_{standard} - 1) \times 1000$$

where $R''_{sample}$ is the ratio of $^{13}C$ to $^{12}C$ in the benzene or xylene; and $R''_{standard}$ is the ration of the natural abundance of $^{13}C$ to the natural abundance of $^{12}C$ (which is equal to 0.01109/0.98891), then the following apply:

Benzene produced according to the present process comprises deuterium and $^{13}C$ in amounts such that δ(deuterium) for the benzene is less than −250, preferably greater than −450 and less than −250, and δ($^{13}C$) for the benzene is less than −24, preferably greater than −59 and less than −24.

Xylene produced according to the present process comprises deuterium and $^{13}C$ in amounts such that the δ(deuterium) value is less than −250, preferably greater than −450 and less than −250, or the δ($^{13}C$) value is less than −24, preferably greater than −60 and less than −24.

The isotopic compositions may also be calculated for various derivatives of the benzene and xylene produced according to the invention. The results are shown in Table 4.

TABLE 4

| Component | δ($^{13}C$) | | δ(Deuterium) | |
| --- | --- | --- | --- | --- |
| | Low | High | Low | High |
| Ethylbenzene | −60 | −22 | −450 | −213 |
| Cumene | −60 | −21 | −450 | −175 |
| Styrene | −60 | −22 | −450 | −213 |
| Polystyrene | −60 | −22 | −450 | −213 |
| Polyethylene Terephthalate | −57 | −22 | −400 | −175 |
| Phenol | −59 | −24 | −433 | −225 |
| Cyclohexane | −59 | −24 | −450 | −175 |
| Nylon6,6 | −52 | −19 | −400 | −138 |
| Toluene | −59 | −24 | −450 | −250 |

It is to be understood the entirety of ranges shown in Table 4 are included in the scope of this invention that is the polystyrene having any combination of a δ($^{13}C$) value of about −60, −59, −58, −57, −56, −55, −54, −53, −52, −51, −50, −49, −48, −47, −46, −45, −44, −42, −40, −38, −36, −34, −32, −30, −28, −26, −24, or −22; and a δ(deuterium) value of about −450, −440, −430, −420, −410, −400, −390, −380, −370, −360, −350, −340, −330, −320, −310, −300, −290, −280, −270, −260, −250, −240, −230, −220, or −213.

It is to be understood the entirety of ranges shown in Table 4 are included in the scope of this invention that is the polyethylene terephthalate having any combination of a δ($^{13}C$) value of about −52, −51, −50, −49, −48, −47, −46, −45, −44, −42, −40, −38, −36, −34, −32, −30, −28, −26, −24, −22, −20, or, −19; and a δ(deuterium) value of about −400, −390, −380, −370, −360, −350, −340, −330, −320, −310, −300, −290, −280, −270, −260, −250, −240, −230, −220, or −210, −200, −190, −180, or −175.

It is to be understood the entirety of ranges shown in Table 4 are included in the scope of this invention that is the nylon having any combination of a δ($^{13}C$) value of about −57, −56, −55, −54, −53, −52, −51, −50, −49, −48, −47, −46, −45, −44, −42, −40, −38, −36, −34, −32, −30, −28, −26, −24, or −22; and a δ(deuterium) value of about −400, −390, −380, −370, −360, −350, −340, −330, −320, −310, −300, −290, −280, −270, −260, −250, −240, −230, −220, or −210, −200, −190, −180, −170, −160, −150, −140, or −138.

In another embodiment, the measured isotope distribution of an aromatic hydrocarbon may be used to identify the type of manufacturing process that was used in its production. Thus, for example, a sample of benzene of unknown origin with a measured δ(deuterium) value of less than −250 and a δ($^{13}C$) value of less than −32 could be uniquely identified as originating from a methane dehydroaromatization process as opposed to a naphtha reforming process. This novel ability to identify the production process of an aromatic hydrocarbon is based on the realization that the amounts of deuterium and $^{13}C$ present in an aromatic hydrocarbon product can serve to differentiate between an aromatic hydrocarbon produced from naphtha, the same aromatic hydrocarbon produced by dehydroaromatization of naturally-occurring geologic methane alone and the same aromatic hydrocarbon produced by dehydroaromatization of naturally-occurring geologic methane and methane produced from $CO_2$.

Furthermore more detailed analytical techniques may utilized to determine molecular locations of $^{13}C$ and deuterium i.e., as part of the ring structure or as part of a alkyl side branch. The analysis of isotope location may be further utilized to differentiate the products of the current invention.

Additional discussion of isotope distribution can be found in U.S. Published Patent Application No. 2007/282145.

In addition, the present invention can result in LNG enriched in $^{13}C$ and Deuterium when compared with the LNG that would be produced from a given gas reservoir utilizing conventional gas liquefaction; that is to say gas liquefaction that is not integrated with the process of methane dehydroaromatization to produce aromatics. This result is due to a recognition by the inventors that—during the dehydroaromatization reaction—methane molecules that contain $^{13}C$ and/or Deuterium are less reactive than those methane molecules that are composed entirely of $^{12}C$ and $^{1}H$; therefore—for a partial conversion process configuration—the lighter isotopes will preferentially be converted to aromatic products and heavier isotopes will preferential remain as methane and end up in the LNG product.

While the illustrative embodiments of the invention have been described with particularity, it will be understood that various other modifications will be apparent to and can be readily made by those skilled in the art without departing from the spirit and scope of the invention. Preferred embodiments include: a process for converting one or more gaseous hydrocarbon streams comprising methane to an aromatic hydrocarbon comprising:

(a) passing at least one gaseous hydrocarbon stream comprising methane to at least one conversion zone and contacting said stream with at least one dehydroaromatization catalyst in said zone under conversion conditions to produce a gaseous product stream comprising at least one aromatic compound and $H_2$;

(b) separating said gaseous product stream into a stream comprising said at least one aromatic compound and a stream comprising methane and $H_2$;

the improvement comprising combining said process with (i) at least one step and/or at least one apparatus and/or at least one process stream in the production, transportation, or use of liquefied natural gas (LNG); and/or (ii) the use of associated gas (which in embodiments may be characterized as containing >5 mol % higher hydrocarbons, for instance greater than 5 mol % C2-C5 hydrocarbons, still more particularly >5 mol % higher hydrocarbons selected from ethane, propane, butanes, and mixtures thereof); and more preferred embodiments including: wherein said at least one step and/or at least one apparatus and or at least one process stream is selected from the group consisting of cryogenic refrigeration apparatus, at least one compressor, and/or BOG stream, and at least one process step, said at least one process step selected from warming or cooling at least one gas selected from the group consisting of natural gas, associated gas, and BOG; and/or where said process further includes a step of separating said stream comprising methane and $H_2$ by cryogenic separation to provide a stream comprising liquid methane (i.e., a stream enriched in liquid methane) and a stream comprising gaseous $H_2$ (i.e., a stream enriched in $H_2$), (these streams readily separated by methods per se known in the art) then sending at least a portion of said liquid methane to disposition as LNG ("disposition" meaning the desired end use or uses of LNG), optionally including a step of removing at least one impurity selected from CO, CO2, O2, $N_2$, and olefins from said liquid methane and/or a step of decompressing said liquid methane; and/or wherein the process further includes a step of separating said stream comprising methane and $H_2$ by cryogenic separation to provide liquid methane and gaseous $H_2$; wherein said cryogenic separation is combined with a step of warming a stream of LNG; and/or the process further characterized by, prior to step (a), said gaseous hydrocarbon stream comprising methane is split into a first gaseous hydrocarbon stream and a second gaseous hydrocarbon stream, wherein said first gaseous hydrocarbon stream is processed according to steps (a) and (b), followed by separation of said gaseous stream of methane and hydrogen by cryogenic separation into liquid methane and gaseous hydrogen; and passing said second portion of said gaseous hydrocarbon stream to a liquefaction process to provide a stream of LNG; the process characterized in that at least one of said cryogenic separation and said liquefaction shares a common refrigeration utility as at least one step and/or at least one process stream in the production, transportation, or use of LNG; and/or wherein said gaseous hydrocarbon stream comprises BOG; and/or wherein said gaseous hydrocarbon stream is associated gas (which for the purposes of the present invention is gas associated with oil, e.g., on top of oil in the oil well, typically comprising higher hydrocarbons as well as methane, e.g., ethane, propane, butanes, and the like); and/or wherein said gaseous hydrocarbon stream comprising methane in step (a) is provided by gasifying LNG and wherein said gasifying is used to provide refrigeration for cryogenic separation of methane and $H_2$; and/or wherein said gaseous hydrocarbon feedstream is further characterized as including methane and at least 10 mol %, preferably greater than 50 mol %, of non-aromatic higher hydrocarbons (such as might be the case with associated gas), based on the total moles of hydrocarbons in said feedstream, and wherein said gaseous product stream is further characterized as comprising at least one aromatic compound, $H_2$, and less than 5 mol %, preferably less than 1 mol %, of said non-aromatic higher hydrocarbons, wherein in certain preferred embodiments the gaseous hydrocarbon feedstream is still further characterized as comprising higher non-aromatic hydrocarbons, and further including a step of separating said stream comprising methane and $H_2$ by cryogenic separation to provide liquid methane and gaseous $H_2$; then sending said liquid methane to disposition as LNG, optionally including a step of removing at least one impurity selected from CO, CO2, O2, N2, and olefins from said liquid methane and/or a step of decompressing said liquid methane; and/or in the case where gaseous $H_2$ is separated from liquid methane, a step of purifying said $H_2$ stream by use of a membrane and/or pressure swing adsorption; and/or wherein said at least one aromatic compound (in any of the embodiments described herein) is selected from benzene, toluene, naphthalene, and mixtures thereof, and wherein in the case where said at least one aromatic compound comprises at least one of benzene and toluene, the process of the invention may further including a step of alkylation to provide xylenes (and still further processing downstream by methods per se known in the art to make products such as PET, nylon, and the like, based on xylenes); and/or also the embodiment where said gaseous hydrocarbon stream further comprises at least one oxygen species selected from the group consisting of water, carbon dioxide, molecular oxygen, carbon monoxide; and/or also the embodiment, wherein methane in said LNG is characterized by an increase in the natural of $C^{13}$ and/or deuterium when compared with the methane contained in said hydrocarbon feed; and/or the embodiment wherein the process further comprising a step of compressing a product downstream of said conversion zone (the aromatization conversion zone) and wherein said compressing shares a common compressor with the production, transportation, or use of liquefied natural gas (LNG); and/or the use of associated gas; and or the use of BOG; and/or also embodiments said stream comprising methane and $H_2$ is separated so as to provide a stream enriched in $H_2$ and a stream enriched in methane, and wherein at least a portion of the $H_2$ in said stream enriched in $H_2$ is used to regenerate said dehydroaromatization catalyst, thereby producing a regenerated dehydroaromatization catalyst and a gas effluent having a reduced level of $H_2$, and optionally then blending CO and/or $CO_2$ with said gas effluent; and/or also for any of the aforementioned embodiments or preferred variations thereof, wherein at least a portion of the $H_2$ in said stream enriched in $H_2$ is used to produce syngas and/or methanol, and/or wherein CO and/or $CO_2$ is added to the stream, which is particularly beneficial when done prior to compression of the $H_2$ to decrease the gas density and/or reduce compression investment. In addition, a preferred embodiment of the invention is a system comprising apparatus for the production of a stream comprising aromatic hydrocarbons from a hydrocarbon stream comprising methane and including a conversion zone for dehydroaromatization of methane and a separation zone for separating said stream comprising aromatic hydrocarbons into at least two streams, one enriched in aromatic hydrocarbons and one comprising unreacted methane and gaseous hydrogen, and apparatus for the production, transportation, or use of liquefied natural gas (LNG), the improvement comprising the integration of said system around a common compressor and/or a common refrigeration system. In additionally preferred embodiments, the invention concerns an integrated process for converting a gaseous hydrocarbon stream comprising methane, to $H_2$ and an aromatic hydrocarbon stream comprising at least one aromatic compound, said process comprising: (a) passing said gaseous hydrocarbon stream to one or more conversion zones containing at least one dehydroaromatization catalyst under conditions suitable for converting methane to said at least one aromatic compound and $H_2$; (b) recovering said aromatic compounds thereby leaving a residual stream comprising gaseous methane and $H_2$; wherein the process is integrated with facilities for the production, transportation, or use of LNG and/or integrated with the utilization of a methane stream containing heavier hydrocarbons. Also there is a preferred embodiment directed to an integrated process for converting a gaseous hydrocarbon stream comprising methane, to LNG, a $H_2$ rich stream, and an aromatic hydrocarbon stream comprising at least one aromatic compound, said process comprising: passing said gaseous hydrocarbon stream to one or more conversion zones containing at least one dehydroaromatization catalyst under conditions suitable for converting methane to said at least one aromatic compound and $H_2$; recovering said aromatic compounds thereby leaving a residual stream comprising gaseous methane and $H_2$; separating said methane and $H_2$ into a gaseous, $H_2$ rich stream and a liquid, methane rich stream; wherein said separating includes cryogenic separation utilizing one or more cryogenic refrigerants; routing said $H_2$ rich stream to a desired disposition with or without further processing; routing said liquid, methane rich stream to an LNG disposition with or without further processing. Moreover, there is a preferred embodiment directed to an integrated process for converting a gaseous hydrocarbon stream comprising methane, to LNG, a $H_2$ rich stream, and an aromatic hydrocarbon stream comprising at least one aromatic compound, said process comprising: passing a first portion of said gaseous hydrocarbon stream to one or more conversion zones containing at least one dehydroaromatization catalyst under conditions suitable for converting methane to said at least one aromatic compound and $H_2$; recovering said aromatic compounds thereby leaving a residual stream comprising gaseous methane and $H_2$; separating said methane and $H_2$ into a $H_2$ rich stream and a methane rich stream; wherein said separating includes cryogenic separation utilizing one or more cryogenic refrigerants; routing said $H_2$ rich stream to a desired disposition with or without further processing; passing a second portion of said gaseous hydrocarbon stream to an LNG liquefaction process utilizing one or more cryogenic refrigerants to produce a liquid methane containing stream; routing said liquid methane containing stream to an LNG disposition with or without further processing; wherein the at least one of the one or more cryogenic refrigerants of (c) and (e) are supplied from the same refrigerant system. Yet another preferred embodiment concerns an integrated process for converting a gaseous stream LNG BOG and/or Jetty BOG gas comprising methane to an aromatic hydrocarbon stream comprising at least one aromatic compound, said process comprising: routing of gaseous stream LNG BOG and/or Jetty BOG gas to a reactor system and if required compressing said gaseous stream to a pressure sufficient to enter a reactor system; passing said gaseous stream to one or more conversion zones containing at least one dehydroaromatization catalyst under conditions suitable for converting methane to $H_2$ and said at least one aromatic compound; recovering said aromatic compounds thereby leaving a residual stream comprising gaseous methane and $H_2$. optional further comprising, compressing said residual methane and $H_2$ stream of (c) and routing said stream to a fuel disposition or other disposition; and/or optional further comprising, recovering at least a portion of the $H_2$ as a $H_2$ rich stream from said stream of methane and $H_2$ after compression and prior to fuel disposition or other disposition. Yet still another preferred embodiment is directed to an integrated process for converting an LNG stream comprising methane to a gaseous hydrocarbon stream comprising methane, an aromatic hydrocarbon stream comprising at least one aromatic compound, and a $H_2$ rich stream, said process comprising: passing said LNG to a heating step where heat is supplied to gasify said LNG, wherein at least a portion of said heat is supplied from integration with the cryogenic separation set forth below; producing a gaseous hydrocarbon stream comprising methane and potentially higher hydrocarbon (e.g., ethane); sending a first portion of the said gaseous hydrocarbon stream to one or more pipelines to convey said stream to one or more consumers of said stream as a fuel or feedstock; sending a second portion of said gaseous stream to one or more conversion zones containing at least one dehydroaromatization catalyst under conditions suitable for converting methane to $H_2$ and said at least one aromatic compound; recovering said aromatic compounds thereby leaving a residual stream comprising gaseous methane and $H_2$; separating said methane and $H_2$ into a $H_2$ rich stream and a methane rich stream; wherein said separating is characterized by cryogenic separation wherein at least a portion of the refrigeration for said cryogenic separation is provided by integration with said gasification of LNG in the first step; routing said $H_2$ rich stream to a desired disposition with or without further processing; routing said methane rich stream to fuel disposition or recycling said methane rich stream to one or more of said conversion zones. Moreover, yet still another preferred embodiment is directed to an integrated process for converting a gaseous feed stream comprising methane and higher hydrocarbons to a gaseous product stream comprising methane and a reduced quantity of higher hydrocarbons, and an aromatic hydrocarbon stream comprising at least one aromatic compound, said process comprising: passing said gaseous stream to one or more conversion zones containing at least one dehydroaromatization catalyst under conditions suitable for converting methane to said at least one aromatic compound; contacting said gaseous stream with said at least one catalyst so as to produce a product stream comprising at least one aromatic compound, $H_2$, and a gaseous hydrocarbon stream comprising methane and a reduced quantity of higher hydrocarbons other than aromatics; recovering said aromatic compounds thereby leaving a residual stream comprising $H_2$, and comprising methane and a reduced quantity of higher hydrocarbons other than aromatics; optionally further comprising, compressing said residual stream of (c) and routing said stream to a fuel disposition; liquefaction to produce LNG, or other disposition; and/or optionally further comprising, recovering at least a portion of the $H_2$ as a $H_2$ rich stream from said stream of methane and $H_2$ after compression and prior to fuel disposition or other disposition wherein said gaseous feed stream of in the first step (the initial feedstream) contains greater than 10 mol % of higher hydrocarbons and said gaseous product stream of the third step (the treated feedstream) contains less than 5 mol % of higher non-aromatic hydrocarbons. In more preferred embodiments of any of the aforementioned integrated processes, in the case where $H_2$ rich streams are produced or utilized, such streams are further purified utilizing a membrane and/or pressure swing adsorption; it is also contemplated that such stream be used in the process to gasify carbon off of the dehydroaromatization catalyst (such as in element 105 of FIG. 1, 205 in FIG. 2, 430 in FIGS. 4, and 505 in FIG. 5), and/or utilized to produce syngas and/or methanol. Also in more preferred embodiments (which may be combined with other preferred embodiments set forth herein), the processes may include one or more steps of: CO removal, $H_2$ removal, $N_2$ removal, olefin removal, and/or addition of higher hydrocarbons to meet LNG product quality specification for contaminant levels and/or heating value. It is yet still another more preferred embodiment of any of the embodiments set forth herein that the recovered aromatic compound is at least one selected from benzene, toluene, and naphthalene; optionally the recovered aromatic compound consists essentially of only one or only two of these aforementioned BTN species, excepting unavoidable impurities. Also, it is a very preferred embodiment of any of the aforementioned embodiments that the process include an addition step of alkylating the benzene and/or toluene produced to produce xylenes; preferably selectively alkylating to produce greater than equilibrium yield of paraxylene. It is also a very preferred embodiment that the abundance of $^{13}C$ and deuterium in the product BTN (or downstream product, e.g., xylene, PET, and the like) and/ or the LNG used downstream be altered from the abundance of these species in the starting material. Another preferred embodiment of any of the aforementioned embodiment is wherein in addition to the gaseous hydrocarbon stream, an oxygen species containing stream is fed to the said one or more conversion zones; wherein said oxygen species is selected from one or more of $H_2O$, $CO_2$, $O_2$, and CO with CO being most preferred. Conversely, there is also a preferred embodiment wherein one or more of said oxygen species is excluded from said one or more conversion zones. In addition, one of the principle advantages of the present invention is that there is an opportunity to use existing compressors to integrate with one or more of the steps provided herein, particularly with respect to existing compressors for the raw Jetty BOG or LNG BOG being integrated with an aromatization process as set forth herein (which may require minor modifications to the compressors within the skill of the routine engineer). Also in very preferred embodiments of any of the aforementioned embodiments, the gaseous feed stream of first fed to the process contains greater than 10 mol %, preferably greater than 50 mol %, of higher hydrocarbons and said gaseous product stream resulting from the one or more conversion zones contains less than 5 mol %, preferably less than 1 mol % of higher non-aromatic hydrocarbons (with any of the higher ranges contemplated with any of the lower ranges).

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. The meanings of terms used herein that have not been defined shall take their ordinary meaning in the art; and if necessary reference shall be taken, in the first instance, to Handbook of Petroleum Refining Processes, Third Edition, Robert A. Meyers, Editor, McGraw-Hill (2004), then to patents and patent applications recited herein.

What is claimed is:

1. A process for converting one or more gaseous hydrocarbon feedstreams comprising methane to an aromatic hydrocarbon comprising:
    (a) passing at least one gaseous hydrocarbon feedstream comprising methane to at least one conversion zone and contacting said stream with at least one dehydroaromatization catalyst in said zone under conversion conditions to produce a gaseous product stream comprising at least one aromatic compound and $H_2$;
    (b) separating said gaseous product stream into a stream comprising said at least one aromatic compound and a stream comprising methane and $H_2$;
    the improvement comprising combining said process with
    (i) at least one step and/or at least one apparatus for warming or cooling or the transportation of liquefied natural gas (LNG); and/or (ii) the use of associated natural gas containing >5 mol % higher hydrocarbons.

2. The process of claim 1, further including a step of separating said stream comprising methane and $H_2$ by cryogenic separation to provide a stream comprising liquid methane and a stream comprising gaseous $H_2$.

3. The process of claim 1, further including a step of separating said stream comprising methane and $H_2$ by cryogenic separation to provide liquid methane and gaseous $H_2$;
    wherein said cryogenic separation is combined with a step of warming a stream of LNG.

4. The process of claim 1, wherein, at least one of the said one or more gaseous hydrocarbon feedstreams is processed according to steps (a) and (b), followed by separation of said gaseous stream of methane and hydrogen by cryogenic separation into liquid methane and gaseous hydrogen; and passing a second portion at least one of the said one or more gaseous hydrocarbon feedstreams to a liquefaction process to provide a stream of LNG; the process characterized in that at least one of said cryogenic separation and said liquefaction shares a common refrigeration utility as at least one step.

5. The process of claim 1, wherein at least one of the said one or more gaseous hydrocarbon feedstreams comprises associated gas, regasified LNG and/or BOG.

6. The process of claim 1, wherein at least one of the said one or more gaseous hydrocarbon feedstreams is still further characterized as comprising higher non-aromatic hydrocarbons, and further including a step of separating said stream comprising methane and $H_2$ by cryogenic separation to provide liquid methane and gaseous $H_2$; then sending said liquid methane to disposition as LNG, and including a step of removing at least one impurity selected from CO, $CO_2$, $O_2$, $N_2$, and olefins from said liquid methane and/or a step of decompressing said liquid methane.

7. The process of claim 1, including a step of separating said stream comprising methane and $H_2$ to provide a methane stream and an $H_2$ stream and then purifying said $H_2$ stream by use of a membrane and/or pressure swing adsorption.

8. The process of claim 1, wherein said at least one aromatic compound is selected from benzene, toluene, naphthalene, and mixtures thereof.

9. The process of claim 1, wherein said at least one aromatic compound comprises at least one of benzene and toluene, and further including a step of alkylation to provide xylenes.

10. The process of claim 1, wherein at least one of the said one or more gaseous hydrocarbon feedstreams further comprises at least one oxygen species selected from the group consisting of water, carbon dioxide, molecular oxygen, carbon monoxide.

11. The process of claim 1, wherein methane in said LNG is characterized by an increase in the natural of $C^{13}$ and/or deuterium when compared with the methane contained in said hydrocarbon feed.

12. The process of claim 1, wherein said stream comprising methane and $H_2$ is separated so as to provide a stream enriched in $H_2$ and a stream enriched in methane, and wherein at least a portion of the $H_2$ in said stream enriched in $H_2$ is used to regenerate said dehydroaromatization catalyst, thereby producing a regenerated dehydroaromatization catalyst and a gas effluent having a reduced level of $H_2$, and optionally then blending CO and/or $CO_2$ with said gas effluent.

13. The process of claim 12, wherein at least a portion of the $H_2$ in said stream enriched in $H_2$ is used to produce syngas.

14. The process of claim 12, wherein at least a portion of the $H_2$ in said stream enriched in $H_2$ is used to produce methanol.

15. The process of claim 1, further including the use of a system comprising apparatus for the production of a stream comprising aromatic hydrocarbons from a hydrocarbon stream comprising methane and including a conversion zone for dehydroaromatization of methane and a separation zone for separating said stream comprising aromatic hydrocarbons into at least two streams, one enriched in aromatic hydrocarbons and one comprising unreacted methane and gaseous hydrogen, and apparatus for the production, transportation, or use of liquefied natural gas (LNG), the improvement in said apparatus comprising the integration of said system around a common compressor and/or a common refrigeration system.

16. The process of claim 15, wherein said integration is around a common compressor.

17. The process of claim 15, wherein said integration is around a common refrigeration system.

18. The process of claim 15, wherein said integration is around a common compressor and a common refrigeration system.

* * * * *